US012714786B2

(12) United States Patent
Mensinger et al.

(10) Patent No.: US 12,714,786 B2
(45) Date of Patent: Aug. 25, 2026

(54) CONTINUOUS GLUCOSE MONITORING TREND-ENABLED DOSE CALCULATOR

(71) Applicant: Companion Medical, Inc., San Diego, CA (US)

(72) Inventors: Michael Mensinger, San Diego, CA (US); Jasper Benke, San Diego, CA (US); Sean Saint, San Diego, CA (US); Jack Pryor, Ladera Ranch, CA (US); Angela Gaetano, San Diego, CA (US)

(73) Assignee: Companion Medical, Inc., San Diego, CA (US)

( * ) Notice: Subject to any disclaimer, the term of this patent is extended or adjusted under 35 U.S.C. 154(b) by 906 days.

(21) Appl. No.: 17/609,747

(22) PCT Filed: May 8, 2020

(86) PCT No.: PCT/US2020/032233
§ 371 (c)(1),
(2) Date: Nov. 8, 2021

(87) PCT Pub. No.: WO2020/231866
PCT Pub. Date: Nov. 19, 2020

(65) Prior Publication Data

US 2022/0211944 A1 Jul. 7, 2022

Related U.S. Application Data

(60) Provisional application No. 62/846,397, filed on May 10, 2019.

(51) Int. Cl.

| | |
|---|---|
| ***A61M 5/172*** | (2006.01) |
| ***G16H 20/17*** | (2018.01) |
| ***G16H 20/60*** | (2018.01) |

(52) U.S. Cl.
CPC .......... *A61M 5/1723* (2013.01); *G16H 20/17* (2018.01); *G16H 20/60* (2018.01);
(Continued)

(58) Field of Classification Search
CPC ........ A61M 5/1723; A61M 2005/1726; A61M 2230/201; A61M 2205/52; A61B 5/145;
(Continued)

(56) References Cited

U.S. PATENT DOCUMENTS

| | | |
|---|---|---|
| 4,755,173 A | 7/1988 | Konopka et al. |
| 5,391,250 A | 2/1995 | Cheney, II et al. |

(Continued)

FOREIGN PATENT DOCUMENTS

| | | |
|---|---|---|
| CN | 107715230 A | 2/2018 |
| WO | 2019075352 A1 | 4/2019 |

OTHER PUBLICATIONS

NIST/SEMATECH e-Handbook of Statistical Methods, http://www.itl.nist.gov/div898/handbook/prc/section2/prc222.htm, (Oct. 16, 2025) (Year: 2012).*

(Continued)

*Primary Examiner* — Michael J Tsai
*Assistant Examiner* — Forrest B Dipert
(74) *Attorney, Agent, or Firm* — Carter, DeLuca & Farrell, LLP

(57) ABSTRACT

Disclosed are systems and methods for determining a dose of insulin that compensates for past carbohydrates consumed, adjusts for blood glucose (BG) trend as well as BG value, and mitigates potential inaccuracies associated with double-counting or overcorrecting, where safeguards are applied to the determination of the insulin dose.

19 Claims, 4 Drawing Sheets

(52) U.S. Cl.
CPC ............... *A61M 2205/3561* (2013.01); *A61M 2205/502* (2013.01); *A61M 2209/01* (2013.01)

(58) Field of Classification Search
CPC ... A61B 5/14532; A61B 5/316; A61B 5/7271; A61B 5/7275; A61B 5/7282; A61B 5/201; G16H 20/10; G16H 20/13; G16H 20/17; G16H 20/60; G16H 20/20
See application file for complete search history.

(56) References Cited

U.S. PATENT DOCUMENTS 5,485,408 A 1/1996 Blomquist
5,522,803 A 6/1996 Teissen-Simony
5,665,065 A 9/1997 Colman et al.
5,800,420 A 9/1998 Gross et al.
5,807,375 A 9/1998 Gross et al.
5,925,021 A 7/1999 Castellano et al.
5,954,643 A 9/1999 Antwerp et al.
6,017,328 A 1/2000 Fischell et al.
6,186,982 B1 2/2001 Gross et al.
6,246,992 B1 6/2001 Brown
6,248,067 B1 6/2001 Causey, III et al.
6,248,093 B1 6/2001 Moberg
6,355,021 B1 3/2002 Nielsen et al.
6,379,301 B1 4/2002 Worthington et al.
6,544,212 B2 4/2003 Galley et al.
6,558,351 B1 5/2003 Steil et al.
6,591,876 B2 7/2003 Safabash
6,641,533 B2 11/2003 Causey, III et al.
6,736,797 B1 5/2004 Larsen et al.
6,749,587 B2 6/2004 Flaherty
6,766,183 B2 7/2004 Walsh et al.
6,801,420 B2 10/2004 Talbot et al.
6,804,544 B2 10/2004 Van Antwerp et al.
7,003,336 B2 2/2006 Holker et al.
7,029,444 B2 4/2006 Shin et al.
7,066,909 B1 6/2006 Peter et al.
7,137,964 B2 11/2006 Flaherty
7,303,549 B2 12/2007 Flaherty et al.
7,399,277 B2 7/2008 Saidara et al.
7,442,186 B2 10/2008 Blomquist
7,602,310 B2 10/2009 Mann et al.
7,647,237 B2 1/2010 Malave et al.
7,699,807 B2 4/2010 Faust et al.
7,727,148 B2 6/2010 Talbot et al.
7,785,313 B2 8/2010 Mastrototaro
7,806,886 B2 10/2010 Kanderian, Jr. et al.
7,819,843 B2 10/2010 Mann et al.
7,828,764 B2 11/2010 Moberg et al.
7,879,010 B2 2/2011 Nunn et al.
7,890,295 B2 2/2011 Shin et al.
7,892,206 B2 2/2011 Moberg et al.
7,892,748 B2 2/2011 Norrild et al.
7,901,394 B2 3/2011 Ireland et al.
7,942,844 B2 5/2011 Moberg et al.
7,946,985 B2 5/2011 Mastrototaro et al.
7,955,305 B2 6/2011 Moberg et al.
7,963,954 B2 6/2011 Kavazov
7,977,112 B2 7/2011 Burke et al.
7,979,259 B2 7/2011 Brown
7,985,330 B2 7/2011 Wang et al.
8,024,201 B2 9/2011 Brown
8,100,852 B2 1/2012 Moberg et al.
8,114,268 B2 2/2012 Wang et al.
8,114,269 B2 2/2012 Cooper et al.
8,137,314 B2 3/2012 Mounce et al.
8,181,849 B2 5/2012 Bazargan et al.
8,182,462 B2 5/2012 Stoc et al.
8,192,395 B2 6/2012 Estes et al.
8,195,265 B2 6/2012 Goode, Jr. et al.
8,202,250 B2 6/2012 Stutz, Jr.
8,207,859 B2 6/2012 Enegren et al.
8,226,615 B2 7/2012 Bikovsky
8,257,259 B2 9/2012 Brauker et al.
8,267,921 B2 9/2012 Yodfat et al.
8,275,437 B2 9/2012 Brauker et al.
8,277,415 B2 10/2012 Mounce et al.
8,292,849 B2 10/2012 Bobroff et al.
8,298,172 B2 10/2012 Nielsen et al.
8,303,572 B2 11/2012 Adair et al.
8,305,580 B2 11/2012 Aasmul
8,308,679 B2 11/2012 Hanson et al.
8,313,433 B2 11/2012 Cohen et al.
8,318,443 B2 11/2012 Norrild et al.
8,323,250 B2 12/2012 Chong et al.
8,343,092 B2 1/2013 Rush et al.
8,352,011 B2 1/2013 Van Antwerp et al.
8,353,829 B2 1/2013 Say et al.
9,672,328 B2 6/2017 Saint et al.
10,835,727 B2 11/2020 Montalvo et al.
2005/0192494 A1 9/2005 Ginsberg
2007/0123819 A1 5/2007 Mernoe et al.
2010/0160861 A1 6/2010 Causey, III et al.
2014/0039383 A1* 2/2014 Dobbles ............. A61M 5/1723 604/66
2014/0309615 A1 10/2014 Mazlish
2017/0220751 A1 8/2017 Davis et al.
2018/0085532 A1 3/2018 Desborough et al.
2018/0110921 A1 4/2018 Saint et al.
2018/0161498 A1 6/2018 Estes
2018/0200434 A1 7/2018 Mazlish et al.
2018/0200435 A1 7/2018 Mazlish et al.
2018/0353698 A1 12/2018 Saint et al.
2020/0327973 A1 10/2020 Pryor et al.

OTHER PUBLICATIONS

Second Chinese Office Action issued in corresponding Chinese Application No. 202080033902.9 issued May 15, 2024, 13 pages.

International Search Report and Written Opinion issued in corresponding International Application No. PCT/US2020/032233 mailed Aug. 12, 2020, 14 pages.

Extended European Search Report issued in corresponding European Application No. 20806308.1 dated Jan. 2, 2023, 12 pages.

Zeevi et al., "Personalized Nutrition by Prediction of Glycemic Responses", Cell 163, No. 5, Nov. 19, 2015, pp. 1079-1094.

Anonymous: "Glycemic index", Wikipedia, Mar. 29, 2019, pp. 1-10, XP093008144.

Foster-Powell et al., "International Table of Glycemic Index and Glycemic Load Values: 2002", American Journal of Clinical Nutrition, vol. 76, No. 1, Jul. 1, 2022, pp. 5-56.

Communication Pursuant to Article 94(3) EPC issued in corresponding European Application No. 20 806 308.1 dated Oct. 21, 2025, 8 pages.

Kozak Milos: "Project AndroidAPS: BolusWizard.java", Project nightscout / AndroidAPS at github, Feb. 26, 2019 (Feb. 26, 2019), XP093325578, Retrieved from the Internet: URL:https://github.com/nightscout/AndroidAPS/blob/395faa7dc958977796388a2a8bef16ddee935594/app/src/main/java/info/nightscout/androidaps/utils/BolusWizard.java.

* cited by examiner

CONTINUOUS GLUCOSE MONITORING TREND-ENABLED DOSE CALCULATOR

CROSS-REFERENCES TO RELATED APPLICATIONS

The present application is a U.S. National Stage Application filed under 35 U.S.C. § 371(a) of International Patent Application No. PCT/US2020/032233, filed May 8, 2020, which claims priority to and benefit of U.S. Provisional Application No. 62/846,397, filed on May 10, 2019 and titled "CONTINUOUS GLUCOSE MONITORING TREND-ENABLED DOSE CALCULATOR." The entire contents of the aforementioned patent applications are incorporated herein by reference for all purposes.

TECHNICAL FIELD

The present disclosure relates to medicine administering and tracking systems, devices, and methods.

BACKGROUND

Diabetes mellitus, also referred to as diabetes, is a metabolic disease associated with high blood sugar due to insufficient production or use of insulin by the body. Diabetes is widely-spread globally, affecting hundreds of millions of people, and is among the leading causes of death globally. Diabetes has been categorized into three categories or types: Type I, Type II, and gestational diabetes. Type I diabetes is associated with the body's failure to produce sufficient levels of insulin for cells to uptake glucose. Type II diabetes is associated with insulin resistance, in which cells fail to use insulin properly. The third type of diabetes is commonly referred to as gestational diabetes, which can occur during pregnancy when a pregnant woman develops a high blood glucose level. Gestational diabetes can develop into Type II diabetes, but often resolves after the pregnancy.

Diabetes, like other diseases and disorders, often require daily monitoring and/or treatment using medical devices that interact with portable computing and/or communication devices that a patient user may use for managing their medical condition and other purposes.

SUMMARY

The present disclosure describes an example of an intelligent medicine administering system in accordance with the present technology. The system includes a pen device in wireless communication with a mobile computing and communication device of a patient user, also referred to as the user's companion device. The pen device is operable to select, set and/or dispense a dose of the medicine for dispensing. In some implementations, the companion device comprises a smart phone, tablet, and/or wearable computing device, such as a smart watch, smart glasses, etc. In some implementations, the companion device is in communication with other computing devices, such as a laptop and/or desktop computer, a smart television, or network-based server computer. The pen device and/or companion device includes a health management software application ("app") that may be associated with the pen device and other smart health management accessories/devices of the intelligent medicine administering system. In one example embodiment, the pen device and/or the companion device is able to distinguish between a priming event or "prime" and a therapeutic dose or "dose" when medicine is dispensed from the pen device. In one embodiment, the health management app includes an adaptive dose calculator and/or decision support modules to suggest the dose for the patient and provide control over several functionalities of the pen device.

The health management app of the companion device associated with the pen device provides a user interface to allow the user to manage his/her health-related data. In some implementations, for example, the health management app can be configured to control some functionalities of the pen device. In some implementations, for example, the health management app provides an interactive user interface to allow a user to manage settings of the pen device, and settings for the companion device (e.g., smart phone, tablet, or wearable computing device) that can affect the functionality of the system. In implementations, for example, the companion device is an independent portable device that the user may carry on his/her person. In example embodiments of the independent portable companion device, the companion device includes a data processing unit, wireless communication unit to allow the device to communicate with the pen device, and a display unit.

In some implementations, for example, via the user interface of the health management app, the companion device allows the patient to browse a list of previous doses, to view an estimate of current medicament active in the patient's body ("medicament on board") based on calculations performed by a medicine calculation module of the health management app, and/or to utilize a dose determination module of the software application to assist the patient regarding dose setting information on the size of the next dose to be delivered. For example, the patient may enter carbohydrates to be eaten and current blood sugar, and the companion device would already know insulin on board. Using these parameters, a suggested medicine dose (e.g., such as insulin dose), calculated by the dose determination module, may be determined.

Disclosed are systems and methods for calculating a specific dose of insulin that compensates for past carbohydrates (carbs) consumed for a properly balanced dose calculation, adjusts for blood glucose (BG) trend as well as BG value, takes steps to avoid double-counting BG trend and overcorrecting, applies safeguards to BG trend adjustments to protect against incorrectly set calculation parameters, and optimizes manual glucose monitoring (e.g., by "finger stick" monitors) and continuous glucose monitoring (CGM) scans for BG control and physician reporting.

By way of example, a typical insulin dose calculator may correct for a patient user's current Blood Glucose ("BG") level (e.g. by recommending insulin to lower BG or recommending food to raise BG), may compensate for food presently being eaten (e.g. by recommending insulin to cover the grams of carbohydrate being consumed), and may subtract any insulin already in the user's body from previous doses (e.g., Insulin on Board or "IOB"). The generalized equation is as follows:

$$\text{Insulin Dose Recommendation}=[\text{BG Correction}]+[\text{Carb Cover}]+[\text{IOB}]$$

Each factor in the above equation, for example, is an amount of insulin in Insulin Units (also referred to as IU or U), where:

[BG Correction]=[(Current glucose level in mg/dL)−(Target glucose level in mg/dL)]/(insulin sensitivity factor in mg/dL/U);

[Carb Cover]=(Carbohydrate in grams)/(Insulin to Carb Ratio in grams/U); and

[IOB]=(Remaining units of insulin in patient's body, based on established equations defining nonlinear burndown of past doses, scaled to user's Duration of Insulin Action).

By way of example, in addition to the above insulin dose recommendation equation, the dose calculator module of the health management app of the present disclosure may compensate for the present BG trend, adjusting the calculation based on predicted change in BG. For example, the app may accomplish this by applying a separate trend adjustment factor to the above equation, or by applying the trend adjustment to the current BG to derive a forecasted BG.

In some embodiments, a method is disclosed for determining a dose recommendation (R) of insulin that accounts for glucose trend adjustment. In some embodiments, the method includes producing a recommended insulin dose by processing the parameters as shown in the following equation:

$$R=[\text{BG Correction}]+[\text{Trend Adjust}]+[\text{Carb Cover}]-[\text{IOB}]$$

where, [Trend Adjust]=(Glucose rate of change in mg/dL/minute)×(Projection Time in minutes)/(insulin sensitivity factor in mg/dL/U).

By way of example, Projection Time is a value selected for projecting BG forward. By way of example, the app may be configured to use any suitable time period for the Projection Time.

In some embodiments, the health management app of the intelligent medicine administering system may execute the above method by first receiving and recording the relevant data (e.g. dose size, time, etc.) from the pen device and/or the sensor device (e.g. CGM), performing the calculation embodied in the above equation, and displaying the resulting dose recommendation (R) on the display unit of the companion device and/or a display unit of the pen device.

In some embodiments of the intelligent medicine administering system disclosed herein, the health management app (app) may calculate a recommended dose of insulin that accounts for an estimated unmetabolized amount of carbohydrates consumed by a patient user. For example, the health management app may determine the value for the recommended dose using a complete equation for an insulin dose recommendation (R) that includes estimated unmetabolized carbohydrates, also referred to as "Carbs on Board" (COB), for example as follows:

$$R=[\text{BG Correction}]+[\text{Trend Adjust}]+[\text{Carb Cover}]-[\text{IOB}]+[\text{COB Adjust}]$$

where, [COB Adjust]=(unmetabolized carbohydrates from recent meals in grams)/(Insulin to Carb Ratio in grams/U).

Using this balanced equation, for example, the app accounts for present BG (as calculated or measured by a CGM), rate of change of BG, carbs to be eaten presently (e.g. as communicated by the user through the app user interface), calculated insulin in the patient user's body, and calculated carbs in the patient user's body.

In some embodiments, the app may account for the COB factor by avoiding the presentation of a dose recommendation to the user for a preset period of time following a meal (e.g. 2 hours). By avoiding dose recommendations for 2 hours (for example) after a meal, or after an inferred or possible meal, the health management app avoids the potential of miscalculating a dose recommendation as a result of unknown carbs remaining in the body.

By way of example, in some embodiments the app may account for the COB factor in the above equation by modeling the user's BG response to a meal with carbs to calculate and assign a COB value. While no general standardized model exists, the app may approximate the effect of carbohydrates and/or assume the worst-case until the app receives information indicating a different result.

In some embodiments, the user may scale the carb burndown rate manually, for example by selecting a qualitative value (e.g. "fast" carbs, "slow" carbs, and the like) from a menu or touch buttons presented by the app on the display unit while using the dose calculator module during a meal time. In some embodiments, the action times corresponding to the qualitative value (e.g. fast and slow carbs) within the app may be pre-set, or configurable by the user or the user's physician.

In some embodiments, the intelligent medicine administering system may determine the burndown rates or curves of specific foods and combinations of foods empirically, for example by aggregating BG response of specific food items across a population of users of the health management app (e.g. for which certain data may be transmitted to/from, and aggregated by, the data processing system of the intelligent medicine administering system). The app may then subtract the expected response from any insulin taken (based on more consistently established burndown curves) and normalize for initial BG and BG trend, to extract the resulting net BG effect of the food or foods. By averaging these curves across many users, the system may derive a generalized model of BG response for a specific food item of combination of food items.

By way of example, in some embodiments, if the carb burndown rate of a meal is not known (e.g., no aggregate response available, and no user selection made), then app may be conservatively configured to default to the fast carbs indication for each meal or food item consumed. A fast carbs indication may cause the app to apply the highest rate of BG change and the fewest remaining carbs on board, conservatively resulting in a low insulin recommendation. Then, during a period of time after the meal, the app may subtract the expected effects of the initial BG value, BG trend, and any insulin administered from the user's actual BG data (e.g. provided to the app from the CGM), resulting in calculation of the net carb response for a particular food item or combination of food items. The app may then analyze the calculated net carb response to derive information about the carbs consumed. For example, the rate of BG change, and the total change of BG level after a period of time may indicate the speed of the carbs (e.g. fast or slow), and therefore the bumdown rate of the carbs consumed and amount remaining (e.g. COB) at the time of analysis. Moreover, in some embodiments the app may curve-fit (e.g. apply to a distribution curve) the net BG response to estimate the true burndown time of the carbs consumed. In some embodiments, the app may use the net BG response to determine a maximum safe assumption limit for the burndown rate of the carbs consumed. For example, if the fastest carbs are assumed to burn down in 15 minutes (e.g. default burndown rate), and CGM data after a certain period of time (e.g. 30 minutes) shows minimal net BG increase, then the app may safely determine that the carb burndown rate for the food item(s) consumed is at least the time elapsed since meal consumption (e.g. 30 minutes). Additionally, the app may recognize the newly determined burndown rate (e.g. 30 minutes) as the maximum safe burndown rate assumption limit for the carbs consumed such that the app may apply this newly determined burndown rate (e.g. 30 minutes) to the recommended dose calculation for any subsequent instance the food item or combination of food items is consumed by the user.

For example, even if the app does not mathematically account for COB in the dose calculator, the COB factor can be used as a backup safety check on dose calculations. For example, the app may consider the carbs being consumed to be fast carbs by default, and run the COB calculation (e.g. secondary dose calculation) in parallel as a safety check with a dose calculation excluding the COB factor (e.g. primary dose calculation). The primary dose calculation may be run using the traditional mathematical formula presented above to achieve target BG. The secondary dose calculation may be run concurrently to predict the worst-case low BG if all carbs were fast, and if the predicted worst-case value falls below an unacceptable threshold then the system may present a warning to the user (e.g. visual and/or audio) and/or adjust the final dose recommendation conservatively to assure safety.

In some embodiments, a method for determining a dose of insulin for a patient is described. In various implementations, the method may be embodied as a set of instructions within the health management app of the intelligent medicine administering system and implemented by a computing device of the system, including but not limited to the pen device, the companion device, and/or a remote computer (e.g., server(s) in the cloud) of the system. By way of example, the method includes a process to determine or receive a blood glucose correction parameter for a patient user of an insulin delivery device. The method further includes a process to determine or receive a carbohydrates cover parameter for the patient user. The method further includes a process to determine or receive an insulin on board (IOB) parameter for the patient user. The method further includes a process to determine or receive a glucose trend adjustment parameter for the patient user. The method further includes a process to determine or receive a carbohydrates on board (COB) adjustment parameter for the patient user. In some embodiments of the method, the COB adjustment parameter includes a quotient of an estimated value for unmetabolized carbohydrates ingested from recent meals by the patient user and an insulin-to-carbohydrates ratio of the patient user. The method further includes a process to produce a recommended dose of insulin based on an estimated sum of the blood glucose correction parameter, the glucose trend adjustment parameter, the carbohydrates cover parameter and the COB adjustment parameter subtracted by the IOB parameter. In some optional embodiments of the method, for example, the method can include a process to display the produced recommended dose of insulin on an insulin delivery device (e.g., pen device) or a mobile device in wireless communication with the insulin delivery device (e.g., companion device).

Implementations of the method can include one or more of the following features. For example, the estimated value for unmetabolized carbohydrates of the COB adjustment parameter can include a fixed time period after a last ingested meal by the patient user. For example, the blood glucose correction parameter can include a difference value between a current glucose level of the patient user and a quotient of a target glucose level and a sensitivity factor of the patient user. For example, the carbohydrates cover parameter can include a quotient of a carbohydrates value and the insulin-to-carbohydrates ratio of the patient user. For example, the IOB parameter can include an estimated value of remaining units of insulin in the patient user's body. For example, the glucose trend adjustment parameter can include a product of an estimated value of a rate of change in glucose levels of the patient user and a quotient of a projection time and an insulin sensitivity factor (ISF) of the patient user.

For example, the estimated value for unmetabolized carbohydrates of the COB adjustment parameter can include a carbohydrates burndown parameter. In some implementations, for example, the carbohydrates burndown parameter includes a variable value associated with the burndown rate, or includes a binary value associated with a fast burndown rate or a slow burndown rate. In some implementations, for example, the carbohydrates burndown parameter includes an estimated value based on a population data for a particular type of food. In some implementations, for example, the carbohydrates burndown parameter is determined by: assigning the carbohydrates burndown parameter at a first predetermined burndown rate associated with a fast metabolic rate of carbohydrate for a first portion of a time period after a last ingested meal by the patient user; and assigning the carbohydrates burndown parameter at a second predetermined burndown rate associated with a slow metabolic rate of carbohydrate for a second portion of the time period. In some implementations, for example, the carbohydrates burndown parameter is determined by: assigning the carbohydrates burndown parameter at a first predetermined burndown rate associated with a fast metabolic rate of carbohydrate for a first portion of a time period after a last ingested meal by the patient user; and assigning the carbohydrates burndown parameter at a second burndown rate, wherein the second bumdown rate is determined based on a net carbohydrates response estimation using an initial blood glucose value, a rate of change of the blood glucose levels over the a portion of the time period, and a current blood glucose value of the patient user.

In some embodiments, the dose calculation module of the app may calculate future values of BG, COB, and IOB. For example, future BG can be projected based on present rate of change, and COB and IOB burndown can be calculated for a future time point instead of the present time. The app may calculate all of these values for a time point in the near future, for example 30 minutes from the time of calculation. By way of example, the generalized equation for a dose recommendation (R) with future values is:

$$R=[\text{Future BG Correction}]+[\text{Carb cover}]-[\text{Future IOB}]+[\text{Future COB Adjust}]$$

where:

[Future BG]=(Present BG in mg/dL)+[(BG Rate of change in mg/dL/min)×(Projection Time in min)]; and

[Future BG Correction]=(Future BG in mg/dL)/(insulin sensitivity factor in mg/dL/U).

In addition to calculating a dose based on a near future projection, the app may simulate all time points to forecast whether a hypoglycemic (or hyperglycemic) excursion is likely within a particular leading time period based upon the user's expected mealtime behavior and BG data communicated to the app from the CGM. By performing near-future projection calculations, the app may detect a potentially dangerous situation and as a result may advise the user to reduce or delay the insulin dose so that BG target can be achieved without allowing BG to dip below a defined safety threshold.

In some embodiments, the app may simulate all time points in a forward time period (e.g. 2 hours) to forecast future BG levels within the defined time period. By way of example, the app may identify the forecasted maximum BG value and/or the forecasted minimum BG value, and then use these values to run a dose recommendation calculation for that future time point marking the identified maximum or minimum to optimize the insulin dose administered. In some embodiments, the app may include safeguards in such a calculation to prevent hypoglycemia, for example by capping the maximum adjustment, re-running the simulation at least once to confirm forecast and check for a projected hypoglycemic response.

A challenge with applying a BG trend correction is that BG trend may be impacted by several different factors affecting the trend in the same direction (e.g. recent insulin dose affects both BG trend and IOB adjustment, and metabolization of carbs affects both BG trend and COB adjustment), resulting in a double-counting or amplification of the trend which may lead to potentially inaccurate dose recommendations. Thus, in some embodiments the app may be configured to differentiate the trend associated with known insulin and carbohydrates from the trend caused by other factors to avoid double-counting the trend and over- or under- correcting with insulin.

Use of a traditional dose calculator is already susceptible to error in settings, but enabling BG trend correction may compound the effect of error. In particular, the settings for Insulin Sensitivity Factor (e.g. amount of insulin required to adjust BG) and Duration of Insulin Action (also referred to as Insulin Action Time; e.g. the rate at which insulin decays in the body, used to calculate IOB) are both critical to properly correcting for BG trends. By way of example, methods are described herein to achieve the most accurate BG control for a user (e.g. by mitigating the risk of compounding error when adjusting the dose calculation for BG trend), where the app 40 can correct for BG and BG Trend, but only if it is safe to do so and will not cause over-correction due to poorly set parameters.

In some embodiments in accordance with the present technology, the disclosed systems and methods may be equipped with a "conservative mode" or a variable parameter of conservatism for a patient user. By way of example, this may be used in cases where insulin parameters are not yet established or trusted (such as for a new user), cases where a user has just changed therapy and is monitoring their body's response, cases where a user may be new to carb counting and prone to mis-estimation, or high-risk cases where hypoglycemia safety is more critical than tight BG control, such as for children, ill patients, or elderly patients.

In some embodiments in accordance with the present technology, the dose calculator module of the app may include an "exercise mode" that adjusts calculations to help a patient user maintain stable and safe BG during exercise.

Some glucose monitoring systems are continuously connected to a user interface (such as a smart phone app), but other systems require manually scanning a sensor to upload data or manually taking a finger stick reading to check BG. In such instances, the health management app 40 may periodically prompt the user for a BG check. Additionally, the health management app may optimize interaction with a user's finger stick BG meter (via user instruction) so the user can take the minimal number of finger stick measurements with the maximum benefit.

BRIEF DESCRIPTION OF THE DRAWINGS

Many advantages of the present disclosure will be apparent to those skilled in the art with a reading of this specification in conjunction with the attached drawings, wherein like reference numerals are applied to like elements and wherein.

DETAILED DESCRIPTION

Figure 1:
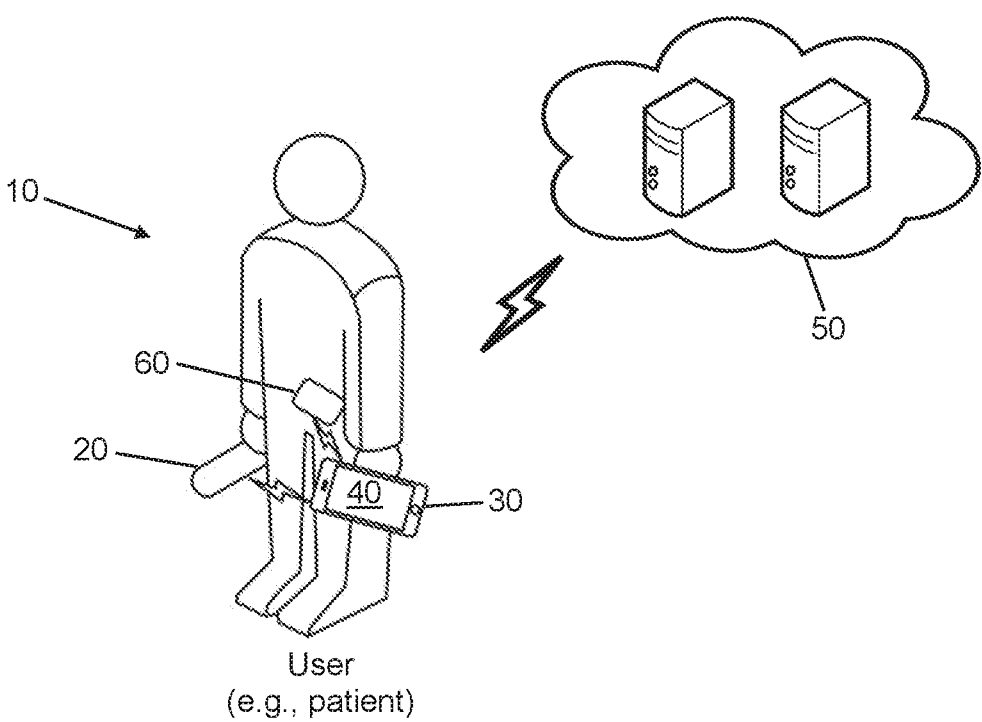
FIG. 1 is a block diagram representing an example of an intelligent medicine administering system according to some embodiments of the disclosure.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The intelligent medication delivery system and related methods disclosed herein boast a variety of features and components that warrant patent protection, both individually and in combination.

Various diseases and medical conditions, such as diabetes, require a patient to self-administer doses of a fluid medication. Typically, when administering a fluid medication, the appropriate dose amount is set and dispensed by the patient using a syringe, a pen, or a pump. For example, self-administered medicaments or medicine include insulin used to treat diabetes, Follistim® used to treat infertility, or other injectable medicines such as Humira®, Enbrel®, Lovenox® and Ovidrel®, or others.

A medicament pen is a device that can be used to inject a quantity of a medicine (e.g., single or multiple boluses or doses of the medicine) into a user's body, where more than one dose can be stored in a medicine cartridge contained in the pen device. Pens offer the benefit of simplicity over other methods of delivery, such as syringe or pump-based methods. For example, syringes typically require more steps to deliver a dose, and pumps typically are more complicated to use and require a constant tether to the patient. However, previously there has not been an automated way to track and communicate the doses given with the pen in a simple, effective and reliable manner. In addition, it can be difficult to know how much to dose with the pen, when to dose, or if the patient dosed at all.

As with the dosing of any medication, it is sometimes hard for a patient to remember if a dose has been given. For this reason, for example, pill reminders have been developed where the patient places the medication for the day in a cup labeled with that day. Once they take their medication, there is no question it has been taken because the pills are no longer in the cup. Yet, there are no widely acceptable solutions that address this problem for injection-based therapies. Therefore, without simple, effective and reliable ways of tracking medicine doses, particularly for managing lifelong or chronic conditions like diabetes, patients may easily miss a dose or administer an incorrect dose (e.g., under-dose or over-dose) of their medicine, which may result in serious, dangerous consequences to their health.

In addition to the challenges of tracking doses, calculating the right dose at the right time or under the right conditions is a widespread problem for patients of chronic conditions requiring daily dosing of medicine. A typical insulin bolus (dose) calculator works by evaluating a diabetic person's (also referred to as "patient") current blood glucose level (BG), the insulin in their body from previous doses (e.g., insulin on board or IOB), and the number of grams of carbohydrates ("carbs") the user is or recently has been eating. From these values and the patient's pre-set clinical parameters, a conventional dose calculator computes an estimated amount of fast-acting insulin to take, based on clinically-validated established equations. Conventional dose calculators for administering insulin for Type I and Type II diabetes typically require manual estimation of carbohydrates ("carbs") at mealtime. For some users, carb-counting and estimating may be too difficult, and some users may not utilize the dose calculator due to the manual work and number of steps required to do so, e.g., taking out one's smartphone, opening up an app, manually typing calculator inputs, etc.

While BG can be measured directly and IOB can be calculated explicitly based on recent insulin doses, the grams of carbs must be manually estimated by the user. This leads to inaccuracy, difficulty in training, and some users being unwilling or unable to use a dose calculator. Yet, for patients, using a dose calculator is much more accurate than the patient roughly estimating or guessing at the proper dose; as such, a dose calculator can contribute to better glycemic control, better safety, and better health. For these reasons, it is desirable for a dose calculator to be used even by people who cannot or will not estimate carbs.

Moreover, conventional bolus or basal insulin dose calculators may operate solely using a pre-set, fixed dosing parameters, as defined by the patient user's physician, that inform the dose calculator. Primary variables of insulin dose are just the user's analyte levels, food intake, and insulin on board. Yet, there are countless other factors that affect the user's glucose and insulin responses, some of which can be incorporated into refined dosing parameters.

One such factor is the diabetic patient's glucose pattern or "trend" over a period of time, e.g., on a daily basis. The glucose trend is the rising or falling of glucose values within a relatively short time period, such as 5 minutes, 15 minutes or 30 minutes. For example, a rapid rise of glucose levels (e.g., from 100 mg/dL to 150 mg/dL over 5 minutes) could be a significant circumstance for the diabetic patient to account for, e.g., as compared to a steady rise from 100 mg/dL to 150 mg/DL over 1 hour. The diabetic patient would typically respond differently in their treatment decision, including using a dose calculator to determine the appropriate dose for such decisions. Yet, such factors are not well recognized by conventional dose calculators, impairing the ability of conventional dose calculators to provide accurate or appropriate dosing information for the patient user's insulin injection device (e.g., pump, pen or other).

Disclosed are systems, devices and methods for calculating a specific dose of insulin that (i) compensates for blood glucose (BG) trend and other factors like past carbohydrates (carbs) consumed for a properly balanced dose calculation, (ii) adjusts for blood glucose (BG) trend in addition to BG value, and (iii) provides safeguards, such as providing BG trend adjustments to protect against incorrectly set calculation parameters. In implementations, the disclosed systems, devices and methods can be used for optimizing manual glucose monitoring (e.g., by "finger stick" monitors) and continuous glucose monitoring (CGM) scans for BG control and physician reporting.

In some embodiments, the disclosed systems, devices and methods include a dose calculator module that can be embodied on a health management software application ("app") resident on (i) a patient user's peripheral medical device, which can include a medicine injection device (also referred to as the "pen" or "pen device") and/or (ii) the patient's "companion" device (e.g., a smartphone, smartwatch, or wearable communication device), which is in data communication with the pen device, and where one or both of which are able to detect and record dose sizes dialed on the pen device and delivered, including the capability of distinguishing between a priming dose and a therapy dose. Communication between the pen device and the companion device provides the ability for dose tracking, logging, calculating, recommending and/or communicating of dose data with a user (e.g., patient user, health care provider (HCP) and/or caregiver), and other advantages of the intelligent medicine administration system. For example, each bolus that is dispensed by the pen device can be automatically logged and communicated to the companion device. In some embodiments, the dose calculator module, or sub-modules thereof, can be resident on a computer system or communication network accessible via the Internet (referred to as 'the cloud') that includes one or more remote computational processing devices (e.g., servers in the cloud).

FIG. 1 shows a diagram of an example embodiment of an intelligent medicine administering system 10 in accordance with the present technology. The system 10 includes a peripheral medical device 20 (e.g. pen device 20) in wireless communication with a mobile computing and communication device 30 of a patient user, also referred to as the user's companion device. The pen device 20 is operable to select, set and/or dispense a dose of the medicine for dispensing. In some implementations, the companion device 30 includes a smart phone, tablet, and/or wearable computing device, such as a smart watch, smart glasses, etc. In some implementations, the companion device 30 is in communication with other computing devices, such as a laptop and/or desktop computer, a smart television, or network-based server computer. The pen device 20 and/or companion device 30 includes a health management app 40 that may be associated with the pen device 20 and other smart health management accessories/devices of the intelligent medicine administering system 10.

In some embodiments, the system 10 includes a data processing system 50 in communication with the companion device 30 and/or the pen device 20. The data processing system 50 can include one or more computing devices in a computer system or communication network accessible via the Internet (also referred to as "the cloud"), e.g., including servers and/or databases in the cloud.

The health management app 40 is paired with the pen device 20, which may be a prescription-only medical device. In some implementations, the pairing (also referred to as bonding) of the companion device 30 to the pen device 20 indicates to the health management application 40 that the user is ready to use all features of the application, which can augment performance and provide important features to the intelligent medicine administering system 10. Thus, in some implementations the act of pairing (bonding) therefore enables the full functionality of the health management app 40. For example, in some cases the pairing may enable the entire app 40, in which at least a portion of the health management app 40 may be disabled without the specialized pairing; whereas in other cases, the pairing may enable certain features of the health management app 40, which otherwise provides some limited features without the specialized pairing.

In some implementations, for example, the health management app 40 can monitor and/or control functionalities of the pen device 20 and track doses (e.g. including priming doses and injection doses) dispensed by the pen device 20 and/or provide a dose calculator and/or decision support modules that can calculate and recommend a dose of the medicine for the patient user to administer using the pen device 20.

The companion device 30 can be used to obtain, process and/or display contextual data that can be used to relate to the patient user's health condition, including the condition for which the pen device 20 is used to treat. In an illustrative example, the companion device 30 is operable to track the patient user's location; the patient user's physical activity including step count, movement distance and/or intensity, estimated calories burned, and/or activity duration; and/or the patient user's interaction pattern with the companion device 30. In some implementations, the app 40 can aggregate and process the contextual data to generate decision support outputs to guide and aid the patient user in using the pen device 20 and/or managing their behavior to promote better health outcomes in treating his/her health condition.

In some embodiments, for example, the system 10 can optionally include a sensor device 60 to monitor one or more health metrics of the patient user. Examples of health metric data monitored by the sensor device 60 include analytes, such as glucose, heart rate, blood pressure, user movement, or other. In some implementations, the sensor device 60 is a wearable sensor device such as a continuous glucose monitor (CGM) to obtain transcutaneous or blood glucose measurements that are processed to produce continuous glucose values. For example, the continuous glucose monitor can include a glucose-processing module implemented on a stand-alone display device and/or implemented on the companion device 30, which processes, stores and displays the continuous glucose values for the patient user.

Figure 2:
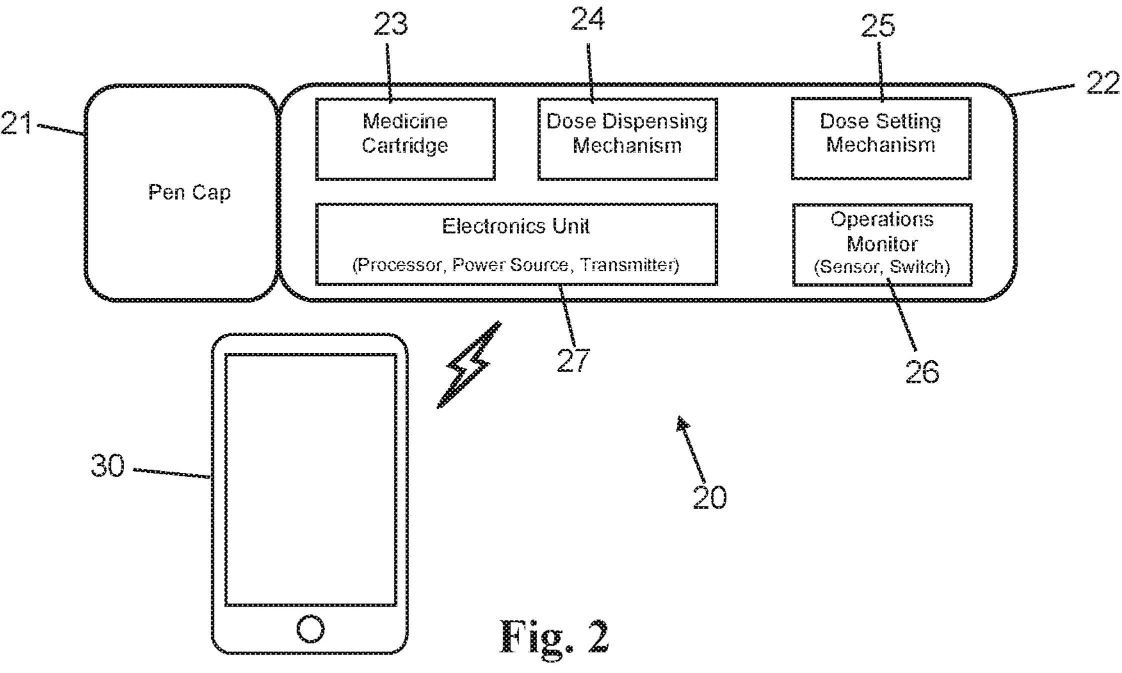
FIG. 2 is a block diagram representing an example of a pen device forming part of the intelligent medicine administering system of FIG. 1.

FIG. 2 shows a diagram of an example embodiment of the pen device 20 of the intelligent medicine administering system 10. The pen device 20 is structured to have a cap 21 configured to protect a medicine dispensing element (not shown) and a body 22 configured to contain the medicine cartridge 23 (e.g., which can be replaceable). The pen device 20 is further structured to include a dose dispensing mechanism 24 to dispense (e.g., deliver) the medicine contained in the medicine cartridge 23 out of the pen device 20, a dose setting mechanism 25 to select and/or set the dose to be dispensed, an operations monitoring mechanism 26 to determine that the pen device 20 is being operated and/or to monitor the operation of the dose being dispensed (e.g., such as a switch and/or sensor, or an encoder), and an electronics unit 27 that can include a processor, a memory, a battery or other power source, and a transmitter. In some embodiments, for example, the pen device 20 may include a display providing a user interface that displays output data (e.g., dialed and/or dispensed dose information, the recommended dose, or other) to a user of the pen device 20. In some embodiments, the display of the pen device 20 may be a touch screen interface that can receive input data from the user.

The pen device 20 is configured in communication with the patient user's mobile computing and communication device 30, e.g., such as the user's smart phone, tablet, and/or wearable computing device, such as a smart watch, smart glasses, etc. and/or a user's laptop and/or desktop computer, a smart television, or network-based server computer.

In some implementations of the system 10, for example, to use the pen device 20, the user first dials up a dose using a dose knob. The dose knob of the pen device 20 can be included as part of the dose setting mechanism 25 and/or the dose dispensing mechanism 24. For example, the dose may be adjusted up or down prior to administration of the dose. When the user applies a force against a dose dispensing button (e.g., presses against the dose dispensing button that is caused to protrude outward from the pen's body upon dialing the dose using the dose knob), a pushing component (e.g., also referred to as a 'plunger') of the dose dispensing mechanism 24 is depressed against an abutment of the medicine cartridge 23 loaded in the pen device 20 to cause the pen device 20 to begin to dispense the medicine, in which the quantity dispensed is in accordance with that set by the dose setting mechanism 25. In such implementations, the operations monitoring mechanism 26 of the pen device 20 will begin to sense movement of a rotating component or shaft that drives the plunger, for example, in which the movement is sensed through an encoder. In some examples, the encoder can be configured to sense the rotation of a component that is coupled to the drive shaft, and as the drive shaft rotates the plunger moves linearly; and therefore, by sensing rotation of the component, the movement of the drive shaft and the plunger is sensed. Movement of the encoder may be detected as data processed by a processor of the electronics unit 27 of the pen device 10, which can be used to measure the dose. In some implementations, the processor can then store the size of the dose along with a time stamp for that dose. In some implementations, the pen device 20 can then transmit the dose and related information to the companion device 30. In such implementations when the dose is transmitted, the data associated with the particular transmitted dose is marked in the memory of the pen device 20 as transmitted. In such implementations if the dose was not yet transmitted to the companion device 30, then the data associated with the dose will be transmitted at the next time a successful communication link between the pen device 10 and the companion device 30 is established.

The operations monitoring mechanism 26 of the pen device 20 can include a sensor that can utilize any method of sensing rotary or linear movement. Non-limiting examples of such sensors include rotary and linear encoders, Hall effect and other magnetic based sensors, linearly variable displacement transducers, or any other appropriate method of sensing known in the art.

The dose dispensing mechanism 24 of the pen device 20 can include a manually powered mechanism or a motorized mechanism. In either case, a force (e.g., either produced by the patient or by an electrically-powered motor) pushes on the plunger of the dose dispensing mechanism 24 to in turn force a receiving plunger of the medicament vial or cartridge 23 to deliver the specific amount of the medicament. In some implementations, for example, the dose dispensing mechanism 24 can be adjusted to deliver the dose over a different period of time. In one example, the dose dispensing mechanism 24 can be operated such that the plunger is pushed in by an adjustable tension spring or change the speed of the motor to inject the dose over a time frame (e.g., 1 s, 5 s or other) to aid in reducing the pain of dosing. In one example, the dose dispensing mechanism 24 can be operated over a much longer period of time, e.g., to better match the dynamics of carbohydrates, which can be like an extended bolus with a pump.

The health management app 40 of the companion device 30 associated with the pen device 20 provides a user interface to allow the user to manage his/her health-related data. In some implementations, for example, the health management app 40 can be configured to control some functionalities of the pen device 20. In some implementations, for example, the health management app 40 provides an interactive user interface to allow a user to manage settings of the pen device 20, and settings for the companion device 30 (e.g., smart phone, tablet, or wearable computing device) that can affect the functionality of the system 10. In implementations, for example, the companion device 30 is an independent portable device that the user may carry on his/her person. In example embodiments of the independent portable companion device 30, the companion device 30 includes a data processing unit, wireless communication unit to allow the device to communicate with the pen device 20, and a display unit.

Figure 3:
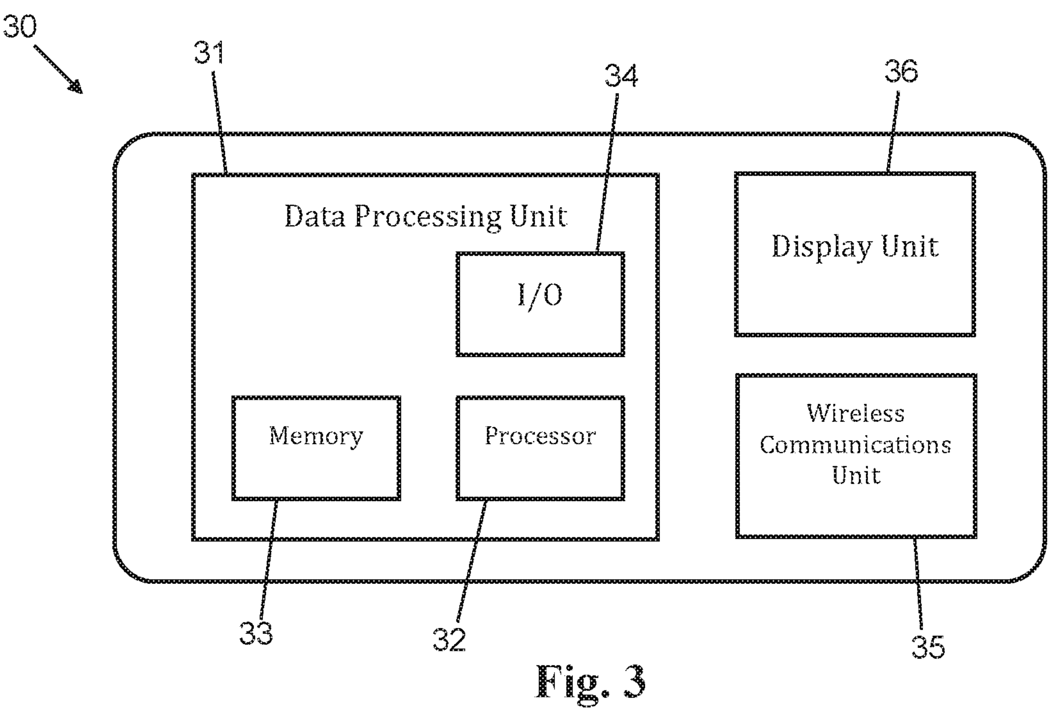
FIG. 3 is a block diagram representing an example of the companion device of the intelligent medicine administering system of FIG. 1.

FIG. 3 shows a block diagram of an example embodiment of the companion device 30 of the intelligent medicine administering system 10. The data processing unit 31 of the companion device 30 includes a processor 32 to process data, a memory unit 33 in communication with the processor 32 to store data, and an input/output unit (I/0) 34 to interface the processor 32 and/or memory 33 to other modules, units or devices of the companion device 30 or external devices. For example, the processor 32 can include a central processing unit (CPU) or a microcontroller unit (MCU). For example, the memory 33 can include and store processor-executable code, which when executed by the processor 32, configures the data processing unit 31 to perform various operations, e.g., such as receiving information, commands, and/or data, processing information and data, and transmitting or providing information/data to another device. In some implementations, the data processing unit can transmit raw or processed data to a computer system or communication network accessible via the Internet (referred to as 'the cloud') that includes one or more remote computational processing devices (e.g., servers in the cloud). To support various functions of the data processing unit, the memory 33 can store information and data, such as instructions, software, values, images, and other data processed or referenced by the processor 32. For example, various types of Random Access Memory (RAM) devices, Read Only Memory (ROM) devices, Flash Memory devices, and other suitable storage media can be used to implement storage functions of the memory unit 33. The I/O 34 of the data processing unit 31 can interface the data processing unit 31 with the wireless communications unit 35 to utilize various types of wired or wireless interfaces compatible with typical data communication standards, for example, which can be used in communications of the data processing unit 31 with other devices such as the pen device 20, via a wireless transmitter/receiver (Tx/Rx) unit, e.g., including, but not limited to, Bluetooth, Bluetooth low energy, Zigbee, IEEE 802.11, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE cellular communication methods, NFC (Near Field Communication), and parallel interfaces. The I/O 34 of the data processing unit 31 can also interface with other external interfaces, sources of data storage, and/or visual or audio display devices, etc. to retrieve and transfer data and information that can be processed by the processor 32, stored in the memory unit 33, or exhibited on an output unit of the companion device 30 or an external device. For example, a display unit 36 of the companion device 30 can be configured to be in data communication with the data processing unit 31, e.g., via the I/O 34, to provide a visual display, an audio display, and/or other sensory display that produces the user interface of the health management application 40. In some examples, the display unit 36 can include various types of screen displays, speakers, or printing interfaces, e.g., including but not limited to, light emitting diode (LED), or liquid crystal display (LCD) monitor or screen, cathode ray tube (CRT) as a visual display; audio signal transducer apparatuses as an audio display; and/or toner, liquid inkjet, solid ink, dye sublimation, inkless (e.g., such as thermal or UV) printing apparatuses, etc.

By way of example, when a dosing event occurs (e.g., an amount of fluid is dispensed from the pen device 20), a time stamp associated with the dosing event is recorded by the processing unit of the pen device 20 (e.g., stored in the memory of the pen device 20). For example, the time stamp may be the current time or a time where a count-up timer is used. When the dose information is eventually transmitted to the health management app 40 of the companion device 30, the time stamp and/or a 'time-since-dose' parameter is transmitted by the pen device 20 and received by the companion device 30 and stored in the memory 33 of the data processing unit 31 of the companion device 30, In some implementations, for example, the time of the dose can be determined without the pen device 20 having to know the current time. This can simplify operation and setup of the pen device 20. In some implementations, for example, a user time is initialized on the pen device 20 from the companion device 30, in which the user time is used for dose time tracking. Using the system 10, the health management app 40 can know the time of the dose relative to the current time.

Once the companion device 30 receives the dose related information (e.g. which can include the time information and dose setting and/or dispensing information, and other information about the pen device 20 related to the dosing event), the companion device 30 stores the dose related information in memory 33, e.g., which can include among a list of doses or dosing events. In some implementations, for example, via the user interface of the health management app 40, the companion device 30 allows the patient to browse a list of previous doses, to view an estimate of current medicament active in the patient's body ("medicament on board") based on calculations performed by a medicine calculation module 74 of the health management app 40, and/or to utilize a dose determination module 75 of the software application to assist the patient regarding dose setting information on the size of the next dose to be delivered. For example, the patient may enter carbohydrates to be eaten and current blood sugar, and the companion device 30 would already know insulin on board. Using these parameters, a suggested medicine dose (e.g., such as insulin dose), calculated by the dose determination module 75, may be determined. In some implementations, for example, the companion device 30 can also allow the patient to manually enter boluses into the pen device 20 or another medicine delivery device. This would be useful if the patient was forced to use a syringe, or if the battery in the pen device 20 was depleted.

Example embodiments and implementations of the disclosed intelligent medicine administering system 10, including the health management app 40 operable on a companion device 30 able to communicate with a medical device (e.g., medicine dispensing device such as a pen device 20), are described. Some examples of features of an intelligent medicine administering system that can be used with the example methods, devices and systems for providing a prescription-regulated software controls on the system are described in U.S. Pat. No. 9,672,328 B2, entitled "Medicine Administering System Including Injection Pen and Companion Device," the entire content of which is incorporated by reference into this disclosure for all purposes.

Figure 4:
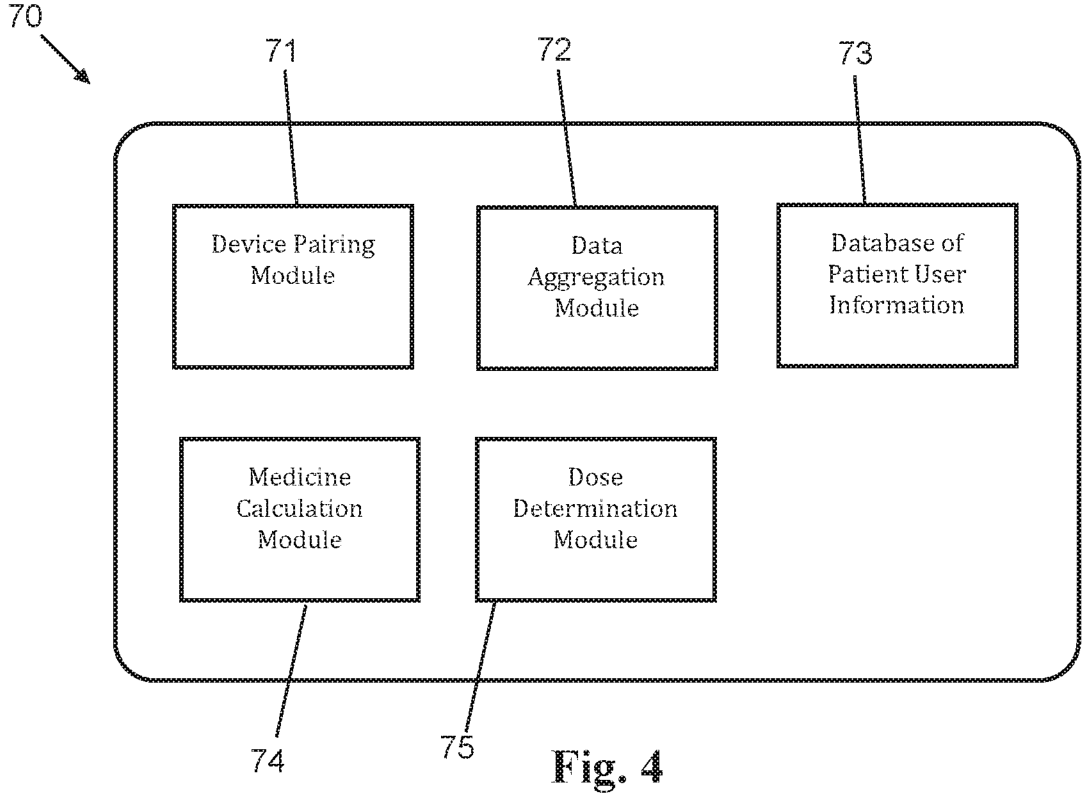
FIG. 4 is a block diagram representing an example of software architecture of data processing modules in accordance with some embodiments of the health management app of the intelligent medicine administrating system of FIG. 1.

FIG. 4 shows a block diagram of a software architecture 70 of data processing modules in accordance with some example embodiments of the health management app 40 of the intelligent medicine administrating system 10. In some embodiments, some or all of the data processing modules of the software architecture 70 of the health management app 40 are resident on the companion device 30. In some implementations of the example software architecture 70, the modules operate to control certain functionalities of the companion device 30, which includes aggregating and processing output signals transmitted by the medical injection device (e.g., pen device 20) to execute a device pairing for validation of the medicine injection device and unlocking of some or all functionality of the health management app 40 on the companion device 30.

In some embodiments of the software architecture 70, some or all of the data processing modules are resident on the companion device 30, e.g., resident in the data processing unit 31. In some embodiments of the software architecture 70 of the system 10, some of the data processing modules can be resident on the pen device 20, e.g., resident in the electronics unit 27. In some embodiments of the software architecture 70 of the system 10, some of the data processing modules may be resident on smart accessories configured for use with standard (non-intelligent) dispensing devices. Similarly, in some embodiments, for example, some of the data processing modules of the software architecture 70 can be embodied as part of a data processing system 50 in the cloud (e.g., resident on one or more cloud computers).

The data processing modules of the health management app 40 on the companion device 30 may include different or the same data processing modules of the software architecture 70 resident on the pen device 20. For example, one of the data processing modules that can be resident on and implemented by the pen device 20 includes a device pairing module 71 to receive and process the output signals from the pen device 20 to pair with the health management app 40 resident on the companion device 30.

In some implementations, the pen device 20 can be paired to the companion device 30 to enable some or all protected features of the health management app 40 associated with a specific user of the pen device 20 and/or data management on the companion device 30 which require secure access for use by the patient user. The secure pairing methods ensure that the health management app 40 resident on the companion device 30 is specifically associated with a particular pen device 20 belonging to the patient user, e.g., who may have a prescription corresponding to use of some or all features of the health management app 40.

In some embodiments of the software architecture 70 for the health management app 40, the data processing modules may also be configured to process health metric data and contextual data obtained by the health management app 40 on the companion device 30, from the pen device 20, from the sensor device 60, and/or from other devices of the patient user and/or apps on the companion device 30. In some embodiments, for example, the software architecture 70 includes a data aggregation module 72 to obtain the health metric data from a device, such as the pen device 20, a sensor device 60, and/or other devices or apps in communication with the companion device 30. The software architecture 70 includes or is in communication with a database 73 to store the health data and contextual data associated with the patient user and populations of patient users. In various embodiments, the database 73 can be resident on the data processing system 60, e.g., in the cloud. In some embodiments, the software architecture 70 includes a medicine calculation module 74 to estimate the current medicament active in the patient's body ("medicament on board" or "insulin on board" or IOB). In some embodiments, the software architecture 70 includes a dose determination module 75, such as a dose calculator module, to autonomously calculate a dose of the medicine associated with dose injections from the pen device 20 based on time-relevant and context or circumstances-relevant data specific to the patient user of the pen device 20. The example modules shown in the software architecture diagram can be organized to provide data to one another in various ways, including directly (e.g., module-to-module) and/or indirectly (e.g., via an intermediary module), based on a periodic, an intermittent and/or a per-request basis.

Figure 5:
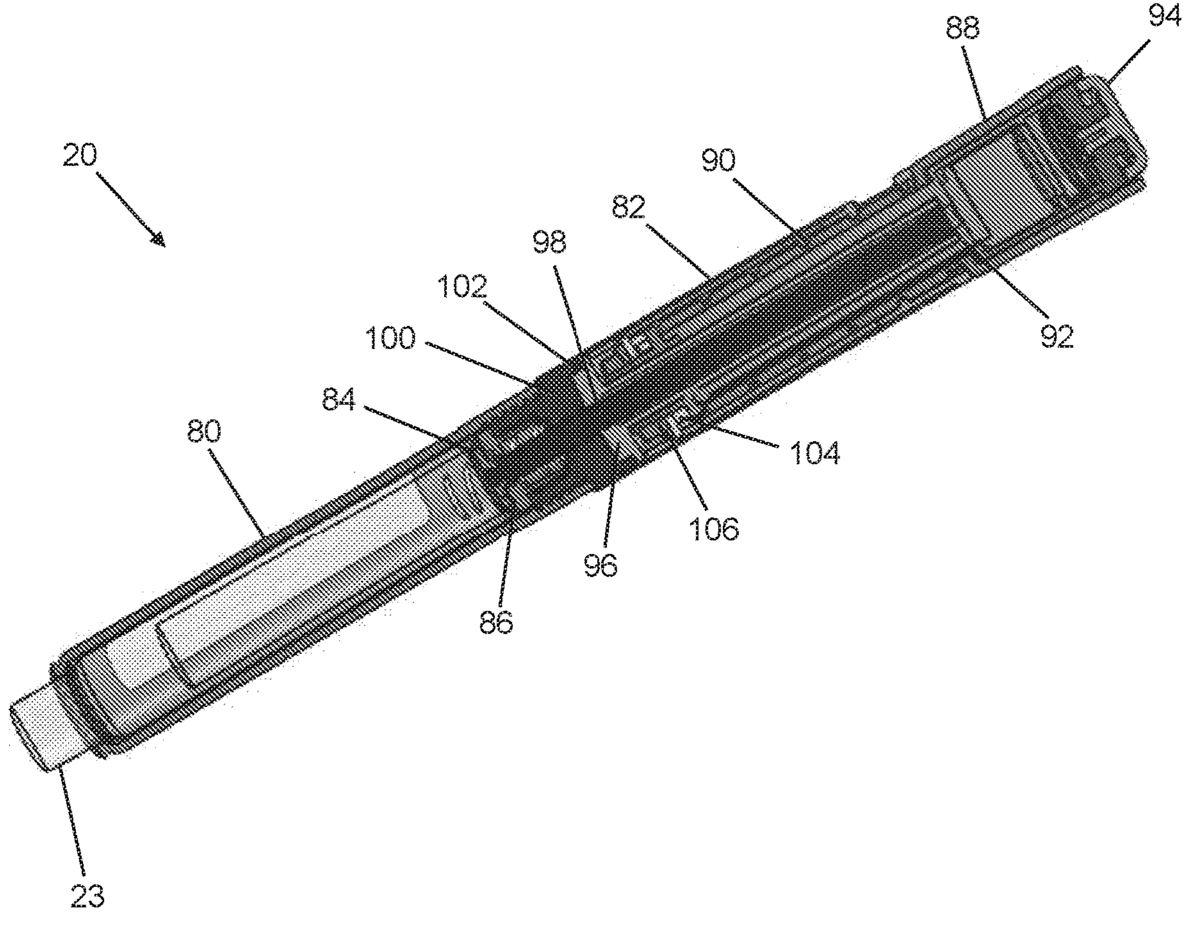
FIG. 5 is a schematic illustration of an example embodiment of the pen device shown in FIG. 2.

FIG. 5 shows a schematic illustration of an example embodiment of the pen device 20. The example shown in FIG. 5 illustrates the structural arrangement and interaction of the example modular units and mechanisms depicted in FIG. 2 for various operations of the pen device 20. As shown in FIG. 5, the pen device 20 of the present example includes a mechanism to actuate a force to cause a displacement of a piston, which resides within a medicament vial or cartridge 23. By way of example, displacement of the piston of the medicament vial 23 forces a volume of the medicament (that is proportional to the displacement of the piston) out of the vial 23, e.g., allowing the medicament to be injected into a patient. The vial 23 is held within a medicament housing 80 of the pen device 20. The medicament housing 80 is attached to a main body housing 82 of the pen device 20, which includes a dose setting and dispensing mechanism and electronics unit of the pen device 20. In some embodiments, for example, the medicament housing 80 and the main body housing 82 may be a singular housing structure. The medicament housing 80 may be structured to include a chamber to hold and/or encase the medicament vial 23 within the housing 80. The pen device 20 may also include a detachable pen cap (not shown) to cover an end of the pen device 20 that exposes a needle assembly (not shown) to disburse the medicine out of the pen device 20 when dispensed from the vial 23. The pen device 20 may include a vial spring 84 that provides a force on a screw retractor 86 to push the medicament vial 23 into the medicament housing 80 to ensure dose accuracy. The pen device 20 includes a dose knob 88 attached to or included as part of the housing 82, where the dose knob 88 is coupled to the housing 82 by a non-self-locking thread 90. In some embodiments, for example, an electronics housing 92 may reside within the dose knob 88, in which the electronics housing 92 contains the electronics unit 27 of the pen device 20. In some embodiments, the dose setting mechanism 25 includes the dose knob 88. When the dose knob 88 is rotated into or out of the housing 82 to adjust the dose, the electronics housing 92 does not turn. However, when translational or axial force is placed to the dose button 94 (e.g., in which resides the electronics housing), a catch structure component is engaged to lock the electronics housing 92 and dose knob 88 together, forcing them to rotate together as the pair travel distally into the housing 82 upon actuation of the dose dispensing mechanism to apply force to the dose knob 88 to cause dispensing of the set dose. The rotation of the dose knob 88, e.g., which can be via the electronics housing 92, rotates a shaft 96 (e.g., which can be configured as a bi-directional clutch shaft). The shaft 96 in turn rotates a dose screw 98, which rides within a nut 100 that is fixed to the housing 82. This rotation causes the dose screw 98 to extend out of the housing 82 causing an injection of medicament. In some embodiments, for example, the dose dispensing mechanism can include a friction-causing structure 102, e.g., which can be coupled to the exemplary bi-directional clutch shaft 96 to present a friction surface (i.e., a surface that provides friction) to make contact with the nut 100 or housing body 82 or other internal structure of the dose dispensing mechanism. The friction surface acts from the bi-directional clutch shaft 96 to the housing 82 or nut 100 to prevent rotation of the shaft 96 while the dose setting mechanism is being adjusted via turning of the dose knob 88, while also allowing the friction to be overcome during the dose dispensing operation. In addition, by overcoming friction in the opposite direction, the dose screw 98 may be driven back into the housing 82 and prepared for a new cartridge of medicament to be loaded. In some embodiments, for example, the pen device 20 includes a screw retractor component 86 that is axially fixed to the housing but rotationally free. The screw retractor component 86 is operable to be bent in to "grab" the non-circular cross section of the dose screw 98 allowing it to be rotated relative to the housing 82 and driven back into the housing 82. In some implementations, for example, the various components of the pen device 20 may be manufactured by injection molding, machining or another similar process. In embodiments including the bi-directional clutch shaft 96, for example, the pen device 20 is capable of allowing retraction of the lead screw, and repeatability of operation of the dose dispensing mechanism.

In some embodiments, the sensor unit of the pen device 20 includes a rotational encoder, for example, between the dose knob 88 (e.g., which can be coupled to the jack screw) and the housing 82, and in electrical communication with the electronics unit 27 contained in the electronics housing 92. The encoder is included in a sensor unit to determine the quantity of the dose set by the dose setting mechanism, and/or, the quantity of the dose dispensed by the dose dispensing mechanism. In some implementations, for example, the encoder may be configured in the pen device 20 to determine the dispensed dose by detecting rotation of the lead screw which is correlated with displacement of the pusher foot which is correlated with displacement of the receiving plunger in the vial 23, which in turn is correlated with dispensed insulin. In some embodiments, for example, the encoder may include two flat plates with contacts in between them. The plates may be aligned perpendicular to a longitudinal axis of the device. For one plate, a contact plate 104 is rotationally fixed to the jack screw, e.g., which can be via the electronics housing 92; and for the other plate, a code wheel 106 is rotationally fixed to the housing 82. In some implementations, for example, when relative motion occurs between these two plates during dosing, the relative motion is measured and transmitted to the data processing and communications unit for processing, storage and/or transmission to the companion device 30.

In some embodiments of the pen device 20, for example, the dose setting and dispensing mechanism may include a mechanism in which the dose screw 98 is comprised of an elongate nut which screws in and out of the housing to provide dosing. The nut component in the previous described embodiment (e.g., nut 100) may include a separate screw structure; whereas in this embodiment of the dose screw, the nut component is part of the dose screw including exterior threads and is coupled to the housing 82. When the exemplary bi-directional clutch shaft 96 provides rotation, it operates on the jack screw, e.g., in which the dosing nut in this case threading it out of the housing.

The example embodiments and implementations of the pen device 20 and companion device 30 are described herein for facilitating understanding of some implementations of the various embodiments of the dose calculator module 75 of the health management app 40 in a system, a device and as a method. While the disclosed embodiments described herein are primarily based on diabetes management systems and methods involving an insulin pen, health management app associated with the insulin pen, and/or glucose monitoring devices to facilitate understanding of the underlying concepts, it is understood that the disclosed embodiments can also include treatment of other health conditions using other medications by the pen device (or an alternative peripheral medical device), health management app, and/or monitoring of other analytes by sensor devices.

Dose Calculation with Adjustment for CGM Trend

By way of example, a typical insulin dose calculator may correct for a patient user's current Blood Glucose ("BG") level (e.g. by recommending insulin to lower BG or recommending food to raise BG), may compensate for food presently being eaten (e.g. by recommending insulin to cover the grams of carbohydrate being consumed), and may subtract any insulin already in the user's body from previous doses (e.g., Insulin on Board or "IOB"). The generalized equation is as follows:

$$\text{Insulin Dose Recommendation}=[\text{BG Correction}]+[\text{Carb Cover}]-[\text{IOB}]$$

Each factor in the equation is an amount of insulin in Insulin Units (also referred to as IU or U), where:

[BG Correction]=[(Current glucose level in mg/dL)−(Target glucose level in mg/dL)]/(insulin sensitivity factor in mg/dL/U);

[Carb Cover]=(Carbohydrate in grams)/(Insulin to Carb Ratio in grams/U);

[IOB]=(Remaining units of insulin in patient's body, based on established equations defining nonlinear burndown of past doses, scaled to user's Duration of Insulin Action).

Other units such as mmol may be used, but the calculations are the same.

By way of example, in addition to the above insulin dose recommendation equation, the dose calculator module 75 of the health management app 40 of the present disclosure may compensate for the present BG trend, adjusting the calculation based on predicted change in BG. For example, the app 40 may accomplish this by applying a separate trend adjustment factor to the above equation, or by applying the trend adjustment to the current BG to derive a forecasted BG. Since the goal of an insulin dose calculator is to achieve (or maintain) target BG in the future, adjusting the dose recommendation based on BG trend may help achieve the target glucose level more accurately than only adjusting for the present BG value. Some CGM (Continuous Glucose Monitor) systems report a trend arrow, indicating approximate rate of change of BG. In some embodiments, the app 40 may use this rough trend value directly. In some embodiments, the app 40 may evaluate the raw BG data over a predetermined recent period of time to calculate a more precise rate of BG change, and then use the calculated value in the dose recommendation calculation. In certain instances in which the app 40 determines the BG trend calculation to be unreliable, for example when data is missing or exhibits signs of noise or erratic patient user behavior, the app 40 may adjust the BG trend conservatively or disregard the trend altogether.

In some embodiments, a method is disclosed for determining a dose recommendation (R) of insulin that accounts for glucose trend adjustment. In some embodiments, the method includes producing a recommended insulin dose by processing the parameters as shown in the following equation:

$$R=[\text{BG Correction}]+[\text{Trend Adjust}]+[\text{Carb Cover}]\ [\text{IOB}]$$

where, [Trend Adjust]=(Glucose rate of change in mg/dL/minute)×(Projection Time in minutes)/(insulin sensitivity factor in mg/dL/U).

By way of example, Projection Time is a value selected for projecting BG forward. Given a rate of change that is assumed to remain roughly constant in the near future, multiplying by an amount of time will approximate the expected change in BG over that time. By way of example, the app 40 may be configured to use any suitable time period for the Projection Time. For example, the app 40 may be configured to use 30 minutes as the projection time to forecast the expected change in BG 30 minutes after dose administration. Insulin takes some amount of time to begin affecting BG. For example, in many cases this time may be approximately 30 minutes, so by selecting a Projection Time value of 30 minutes, the app 40 may anticipate the expected change in BG at the time a new dose of insulin may have a significant effect.

By way of example, the health management app 40 of the intelligent medicine administering system 10 may execute the above method by first receiving and recording the relevant data (e.g. dose size, time, etc.) from the pen device 20 and/or the sensor device (e.g. CGM) 60, performing the calculation embodied in the above equation, and displaying the resulting dose recommendation (R) on the display unit 36 of the companion device and/or a display unit of the pen device 20.

Dose Calculation with Carbs on Board

The equations above account for present BG, carbs presently being eaten, and active insulin from recent doses taken, but do not compensate for food recently eaten. If a user properly administers enough insulin to compensate for a meal at the time the meal is consumed, using the above calculation to calculate a dose after a period of time has elapsed since the end of the meal (e.g., 30 minutes later) may show a surplus of insulin still in the body and may not account for the carbs also in the body balancing out the perceived insulin surplus.

In some embodiments of the intelligent medicine administering system 10 disclosed herein, the health management app 40 may calculate a recommended dose of insulin that accounts for an estimated unmetabolized amount of carbohydrates consumed by a patient user. For example, the health management app 40 may determine the value for the recommended dose using a complete equation for an insulin dose recommendation (R) that includes estimated unmetabolized carbohydrates, also referred to as "Carbs on Board" (COB), for example as follows:

$$R=[\text{BG Correction}]+[\text{Trend Adjust}]+[\text{Carb Cover}]-[\text{IOB}]+[\text{COB Adjust}]$$

where, [COB Adjust]=(unmetabolized carbohydrates from recent meals in grams)/(Insulin to Carb Ratio in grams/U).

Using this balanced equation, the app 40 accounts for present BG (as calculated or measured by a CGM 60), rate of change of BG, carbs to be eaten presently (e.g. as communicated by the user through the app 40 user interface), calculated insulin in the patient user's body, and calculated carbs in the patient user's body. While the COB adjustment factor is needed to balance the equation, its exact value may not be known, for example, because carbs may have been incorrectly estimated (e.g. if the user inputs an incorrect value for mealtime carbs) and/or digestion and metabolism time vary by food type, by patient user, and by other factors such as hydration or time of day. Thus, the app 40 may use one or more of several different methods to account for the Carbs on Board or COB factor referenced above.

In some embodiments (by way of example), the app 40 may account for the COB factor by simply avoiding the presentation of a dose recommendation to the user for a preset period of time following a meal. While carbohydrates do not have a generally accepted or standard bumdown rate (e.g., the metabolization rate of COB after carbs are consumed) that is consistent for all people and all foods, an upper time limit may be established within which carbohydrates are typically expected to metabolize, for example two hours. Thus, one simple method of accounting for carbohydrates on board is to avoid giving a dose recommendation for a fixed time period (for example 2 hours) after a meal. A user may manually indicate to the app 40 that a meal was eaten either by logging it explicitly (e.g. by selecting through the user interface a specific meal configuration or individual food items from a database of food items for which the app 40 has nutritional information including carb content) or by entering a number value corresponding to the carb content of food consumed into the dose calculator module 75 via the user interface (e.g. touch-enabled display unit 36 of the companion device 30). The app 40 may also determine that a meal was eaten based on one or more of the following: (a) the dose calculation is occurring during the user's typical meal time, e.g., as programmed into or "learned" by the app 40 based on user behavior, (b) the app 40 receives information related to an increase in the user's current BG level (e.g. as detected by a CGM 60 and communicated to the app 40), (c) the app 40 records the occurrence of an insulin dose administered by the pen device 20 near a meal time, including for example an insulin dose administered without explicit use of the dose calculator module 75 specifying no carbs, and/or any insulin dose administered by the pen device 20. By avoiding dose recommendations for 2 hours after a meal, or after an inferred or possible meal, the health management app 40 avoids the potential of miscalculating a dose recommendation as a result of unknown carbs remaining in the body.

By way of example, in some embodiments the app 40 may account for the COB factor in the above equation by modeling the user's BG response to a meal with carbs to calculate and assign a COB value. While no general standardized model exists, the app 40 may approximate the effect of carbohydrates and/or assume the worst-case until the app 40 receives information indicating a different result.

In some embodiments, the user may scale the carb burndown rate manually, for example by selecting a qualitative value (e.g. "fast" carbs, "slow" carbs, and the like) from a menu or touch buttons presented by the app 40 on the display unit 36 while using the dose calculator module 75 during a meal time. Additionally (or alternatively), by way of example, the user may select specific food items to be consumed from a searchable database within or accessible by the app 40 and populated with common food items (e.g. default basic database), food items the user has previously consumed (e.g. customized database), and/or food items that a population of health management app 40 users have consumed (e.g. crowdsourced database) Food items that are high in carbohydrate and low in dietary fiber (e.g. orange juice, white rice, bagels, etc.) may be indicated as fast carbs, affecting BG quickly, and food items that are low in carbohydrate and/or high in dietary fiber and/or protein (e.g., pizza, beans, dairy, whole grains, nuts, etc.) may be indicated as slow carbs, affecting BG slowly over several hours. In some embodiments, the action times corresponding to the qualitative value (e.g. fast and slow carbs) within the app 40 may be pre-set, or configurable by the user or the user's physician. Additionally, food items in a searchable database may have relevant nutritional information attached including an expected BG response value. In some embodiments, the app 40 may populate the database (e.g. customized database) with learned BG response data corresponding to specific foods consumed to formulate an expected BG response customized to the user based on actual BG response data.

In some embodiments, the intelligent medicine administering system 10 may determine the burndown rates or curves of specific foods and combinations of foods empirically, for example by aggregating BG response of specific food items across a population of users of the health management app 40 (e.g. for which certain data may be transmitted to/from, and aggregated by, the data processing system 50 of the intelligent medicine administering system 10). The app 40 may then subtract the expected response from any insulin taken (based on more consistently established burndown curves) and normalize for initial BG and BG trend, to extract the resulting net BG effect of the food or foods. By averaging these curves across many users, the system 10 may derive a generalized model of BG response for a specific food item of combination of food items.

By way of example, in some embodiments, if the carb burndown rate of a meal is not known (e.g., no aggregate response available, and no user selection made), then app 40 may be conservatively configured to default to the fast carbs indication for each meal or food item consumed. A fast carbs indication may cause the app 40 to apply the highest rate of BG change and the fewest remaining carbs on board, conservatively resulting in a low insulin recommendation. Then, during a period of time after the meal, the app 40 may subtract the expected effects of the initial BG value, BG trend, and any insulin administered from the user's actual BG data (e.g. provided to the app 40 from the CGM 60), resulting in calculation of the net carb response for a particular food item or combination of food items. The app 40 may then analyze the calculated net carb response to derive information about the carbs consumed. For example, the rate of BG change, and the total change of BG level after a period of time may indicate the speed of the carbs (e.g. fast or slow), and therefore the burndown rate of the carbs consumed and amount remaining (e.g. COB) at the time of analysis. Moreover, in some embodiments the app 40 may curve-fit (e.g. apply to a distribution curve) the net BG response to estimate the true burndown time of the carbs consumed. In some embodiments, the app 40 may use the net BG response to determine a maximum safe assumption limit for the burndown rate of the carbs consumed. For example, if the fastest carbs are assumed to bum down in 15 minutes (e.g. default burndown rate), and CGM data after a certain period of time (e.g. 30 minutes) shows minimal net BG increase, then the app 40 may safely determine that the carb burndown rate for the food item(s) consumed is at least the time elapsed since meal consumption (e.g. 30 minutes). Additionally, the app 40 may recognize the newly determined burndown rate (e.g. 30 minutes) as the maximum safe burndown rate assumption limit for the carbs consumed such that the app 40 may apply this newly determined burndown rate (e.g. 30 minutes) to the recommended dose calculation for any subsequent instance the food item or combination of food items is consumed by the user.

For example, even if the app 40 does not mathematically account for COB in the dose calculator, the COB factor can be used as a backup safety check on dose calculations. For example, the app 40 may consider the carbs being consumed to be fast carbs by default, and run the COB calculation (e.g. secondary dose calculation) in parallel as a safety check with a dose calculation excluding the COB factor (e.g. primary dose calculation). The primary dose calculation may be run using the traditional mathematical formula presented above to achieve target BG. The secondary dose calculation may be run concurrently to predict the worst-case low BG if all carbs were fast, and if the predicted worst-case value falls below an unacceptable threshold then the system 10 may present a warning to the user (e.g. visual and/or audio) and/or adjust the final dose recommendation conservatively to assure safety.

Figure 6:
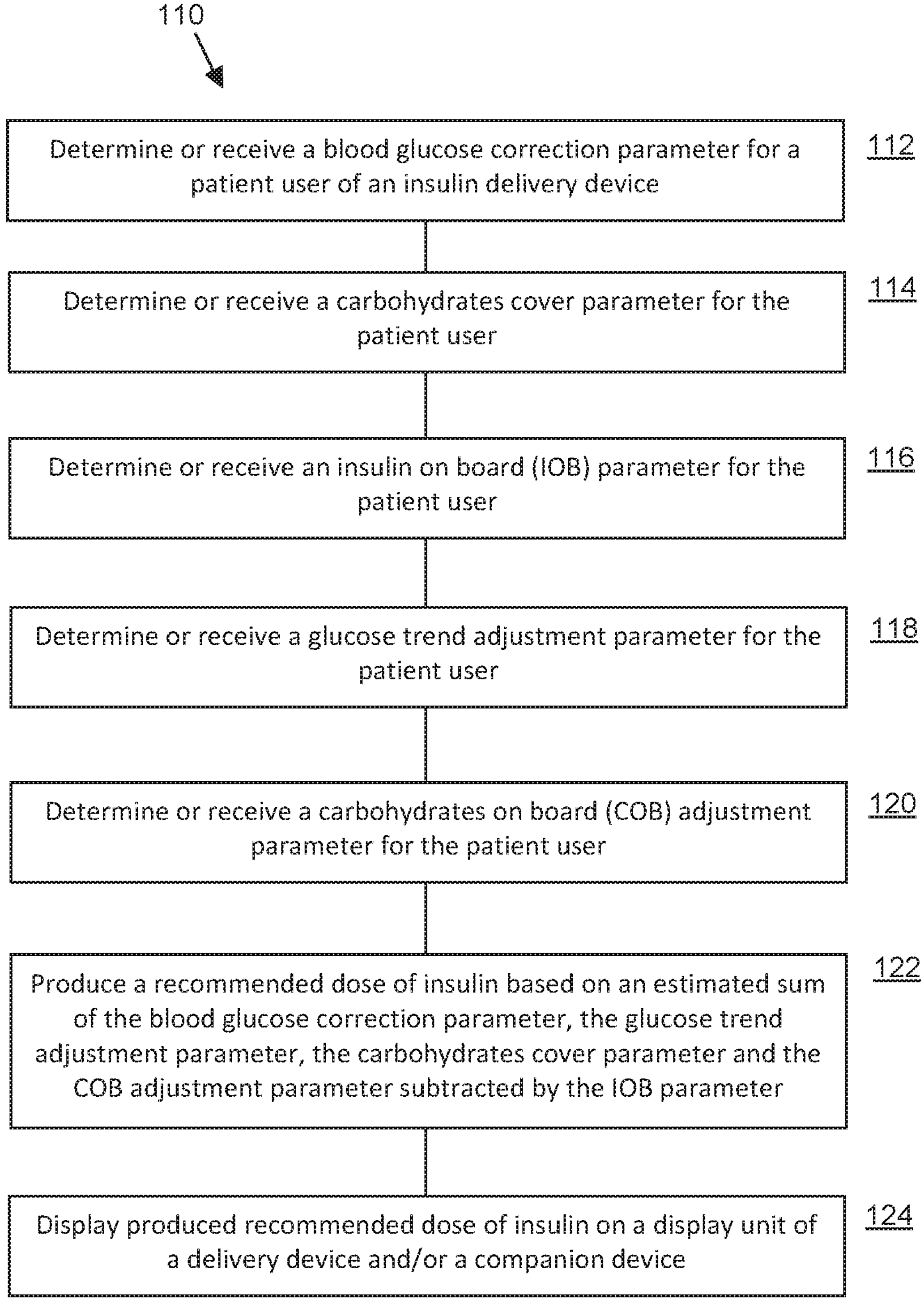
FIG. 6 is a block diagram of an example embodiment of a method for determining a dose of insulin for a patient, in accordance with the present technology.

FIG. 6 shows a block diagram of an example embodiment of a method 110 for determining a dose of insulin for a patient. In various implementations, the method 110 may be embodied as a set of instructions within the health management app 40 of the system 10 and implemented by a computing device of the system 10, including but not limited to the pen device 20, the companion device 30, and/or a remote computer (e.g., server(s) in the cloud) 50 of the system 10. In the example embodiment, the method 110 includes a process 112 to determine or receive a blood glucose correction parameter for a patient user of an insulin delivery device. The method 110 further includes a process 114 to determine or receive a carbohydrates cover parameter for the patient user. The method 110 further includes a process 116 to determine or receive an insulin on board (IOB) parameter for the patient user. The method 110 further includes a process 118 to determine or receive a glucose trend adjustment parameter for the patient user. The method 110 further includes a process 120 to determine or receive a carbohydrates on board (COB) adjustment parameter for the patient user. In some embodiments of the method 110, the COB adjustment parameter includes a quotient of an estimated value for unmetabolized carbohydrates ingested from recent meals by the patient user and an insulin-to-carbohydrates ratio of the patient user. The method 110 further includes a process 122 to produce a recommended dose of insulin based on an estimated sum of the blood glucose correction parameter, the glucose trend adjustment parameter, the carbohydrates cover parameter and the COB adjustment parameter subtracted by the IOB parameter. In some optional embodiments of the method 110, for example, the method can include a process to display the produced recommended dose of insulin on an insulin delivery device (e.g., pen device 20) or a mobile device in wireless communication with the insulin delivery device (e.g., companion device 30).

Implementations of the method 110 can include one or more of the following features. For example, the estimated value for unmetabolized carbohydrates of the COB adjustment parameter can include a fixed time period after a last ingested meal by the patient user. For example, the blood glucose correction parameter can include a difference value between a current glucose level of the patient user and a quotient of a target glucose level and a sensitivity factor of the patient user. For example, the carbohydrates cover parameter can include a quotient of a carbohydrates value and the insulin-to-carbohydrates ratio of the patient user. For example, the IOB parameter can include an estimated value of remaining units of insulin in the patient user's body. For example, the glucose trend adjustment parameter can include a product of an estimated value of a rate of change in glucose levels of the patient user and a quotient of a projection time and an insulin sensitivity factor (ISF) of the patient user.

For example, the estimated value for unmetabolized carbohydrates of the COB adjustment parameter can include a carbohydrates burndown parameter. In some implementations, for example, the carbohydrates burndown parameter includes a variable value associated with the bumdown rate, or includes a binary value associated with a fast burndown rate or a slow burndown rate. In some implementations, for example, the carbohydrates burndown parameter includes an estimated value based on a population data for a particular type of food. In some implementations, for example, the carbohydrates burndown parameter is determined by: assigning the carbohydrates burndown parameter at a first predetermined burndown rate associated with a fast metabolic rate of carbohydrate for a first portion of a time period after a last ingested meal by the patient user; and assigning the carbohydrates burndown parameter at a second predetermined burndown rate associated with a slow metabolic rate of carbohydrate for a second portion of the time period. In some implementations, for example, the carbohydrates burndown parameter is determined by: assigning the carbohydrates burndown parameter at a first predetermined burndown rate associated with a fast metabolic rate of carbohydrate for a first portion of a time period after a last ingested meal by the patient user; and assigning the carbohydrates burndown parameter at a second burndown rate, wherein the second bumdown rate is determined based on a net carbohydrates response estimation using an initial blood glucose value, a rate of change of the blood glucose levels over the a portion of the time period, and a current blood glucose value of the patient user.

Dose Calculation with Future Values

By way of example, an alternate calculation approach that the dose calculation module 75 of the app 40 may employ is to calculate future values of BG, COB, and IOB. For example, future BG can be projected based on present rate of change, and COB and IOB burndown can be calculated for a future time point instead of the present time. The app 40 may calculate all of these values for a time point in the near future, for example 30 minutes from the time of calculation. By way of example, the generalized equation for a dose recommendation (R) with future values is:

$$R=[\text{Future BG Correction}]+[\text{Carb cover}]-[\text{Future IOB}]+[\text{Future COB Adjust}]$$

where

[Future BG]=(Present BG in mg/dL)+[(BG Rate of change in mg/dL/min)×(Projection Time in min)];

[Future BG Correction]=(Future BG in mg/dL)/(insulin sensitivity factor in mg/dL/U)

By way of example, the future COB adjustment factor does not include carbs presently consumed by the user as the calculation is performed, since current carb consumption is accounted for as part of the Carb Cover factor, and any carbs presently consumed by the user should be fully covered by insulin and not presumed to burn down.

In addition to calculating a dose based on a near future projection, the app 40 may simulate all time points to forecast whether a hypoglycemic (or hyperglycemic) excursion is likely within a particular leading time period based upon the user's expected mealtime behavior and BG data communicated to the app 40 from the CGM 60. For example, the app 40 may calculate future projections of BG levels in the leading 2 hours in increments of 5 minutes (or continuously). In situations where slow (or potentially slow, if unknown) carbs are being consumed, fast-acting insulin is being administered, and there is a current downward BG trend and/or current BG is low, even if target BG should be eventually achieved, it is possible that insulin will drop BG before the carbs raise it again, potentially causing a hypoglycemic event. By performing near-future projection calculations, the app 40 may detect a potentially dangerous situation and as a result may advise the user to reduce or delay the insulin dose so that target can be achieved without allowing BG to dip below a defined safety threshold.

In some embodiments, the app 40 may simulate all time points in a forward time period (e.g. 2 hours) to forecast future BG levels within the defined time period. By way of example, the app may identify the forecasted maximum BG value and/or the forecasted minimum BG value, and then use these values to run a dose recommendation calculation for that future time point marking the identified maximum or minimum to optimize the insulin dose administered. In some embodiments, the app 40 may include safeguards in such a calculation to prevent hypoglycemia, for example by capping the maximum adjustment, re-running the simulation at least once to confirm forecast and check for a projected hypoglycemic response.

One consideration for projecting the BG trend or forecasting future BG is whether the user's basal dose (e.g. slow-acting insulin) has been optimized, because un-optimized basal may impose an upward or downward trend on the BG response of the user throughout the day, which would negatively impact trend-including calculations. For example, if the user's basal dose is too high, then the CGM 60 may show BG data indicating a consistent downward trend. Preferably, the user's basal dose can be optimized prior to performing advanced functions such as the trend-enabled dose recommendation calculations disclosed herein. In some embodiments, the app 40 may account for the un-optimized basal effect, for example by subtracting the known or observed trend from the data to normalize the data, and then using the normalized data in advanced functions such as (including but not limited to) dose calculator parameter optimization, meal identification, carb bumdown assessment, assessment of dose calculation success, etc.

In some embodiments, the app 40 may disable advanced functions (or trigger a compensation factor for missed basal dose to account for upward BG trend due to missed basal dose) for which basal dose optimization is critical on any day in which the user misses administering their basal dose, as indicated through manual logging of a missed dose (or failure to manually log the basal dose), or by indication from a smart injector (e.g. pen device 20 of the intelligent medicine administering system 10) or smart accessory (e.g. smart cap). This is because BG trend readings would be affected by a missed basal dose even if the user's basal dose has otherwise been optimized.

Avoiding Double-Counting Trend and IOB/COB

A challenge with applying a BG trend correction is that if the user had recently corrected a high BG with a dose of insulin, their trend will be downward because of the insulin, but IOB will also predict a reduced future BG, which means the trend and the IOB both indicate the same downward BG adjustment in the near future. Compensating for the trend and compensating for IOB may effectively double-count the downward trend and result in too low of a forecasted BG and therefore may cause the app 40 to recommend too little insulin. Similarly, if metabolization of recently consumed carbs are causing an upward BG trend, accounting for the unmetabolized carbs plus the upward trend double-counts the upward trend, resulting in too high of a forecasted BG and therefore the app 40 may recommend too much insulin. It is therefore important to differentiate the trend associated with known insulin and carbohydrates from the trend caused by other factors to avoid double-counting the trend and over- or under- correcting with insulin.

To address the potential of double-counting carbs and/or insulin by accounting for the trend, several methods in accordance with the present technology may be employed by the health management app 40 and are described below.

In some embodiments, the app 40 may include fixed blank-out periods defined after a meal and/or after an insulin dose in which the dose calculator module 75 is disabled. Typically, carbohydrates metabolize within approximately 2 hours, and (fast-acting) insulin acts within approximately 4 hours, so (by way of example) the app 40 may disable the dose calculator for 2 hours following each meal and 4 hours following each insulin dose. When the user has not consumed a meal in the past 2 hours (for example) and has not administered an insulin dose in the past 4 hours (for example), the app 40 may presume the IOB and COB to be zero and carbs and insulin may be presumed by the app 40 not to be affecting BG or BG trend, so the dose calculator module 75 may be used with no compensation. BG and BG trend corrections may be fully applied, and inherently will not be double-counting IOB or COB.

Pediatric patients may have a different time threshold for carbohydrate metabolism, for example 3 hours. The system 10 may allow (or prompt) the user to select the age of the patient or whether they are pediatric and will apply the pediatric time threshold instead of the adult threshold if necessary.

In some embodiments, rather than fully disabling the dose calculator module 75 after a dose or meal, the app 40 may make adjustments to the recommendation calculation for a defined time period (e.g. 2 hours) following a meal and prior to displaying a subsequent dose recommendation, to minimize the risk of double-counting COB and/or IOB. By way of example, in some embodiments the app 40 may perform one or more of the following: (1) Disable the dose calculator module 75 completely; and/or (2) Disable BG correction and use of IOB & COB in the dose calculation, allowing carb covering calculations only; and/or (3) Disable the trend adjustment factor of the dose calculation; and/or (4) Disable compensation for an upward trend, while still compensating for a downward trend; and/or (5) Disable either the use of COB in the calculation or the use of trend correction in the calculation (selecting only one or the other to avoid double-counting); and/or (6) Disable COB or trend correction based on which gives the most conservative (low insulin) value and using that as the final recommendation; and/or (7) Enable trend compensation but use a future forecasted COB value so that the portion of COB responsible for the trend compensation is removed, avoiding double-counting; and/or (8) Subtract the expected BG effect of the meal from the observed BG data (e.g. supplied by the CGM 60), resulting in a net BG response that the food is not responsible for, and using this net response to calculate BG and BG trend corrections such that the carbs are not double-counted.

In some embodiments, in a defined time period (e.g. 4 hours) following an insulin dose, the app 40 may perform one or more of the following (by way of example): (1) Disable the trend adjustment factor of the dose calculation; and/or (2) Disable either the use of IOB in the calculation or the use of trend correction in the calculation (selecting only one or the other to avoid double-counting); and/or (3) Disable IOB or trend correction based on which gives the most conservative (low insulin) value and using that as the final recommendation; and/or (4) Enable trend compensation but use a future forecasted IOB value (based on the modeled burndown behavior) so that the portion of IOB responsible for the trend compensation is removed, avoiding double-counting; and/or (5) Subtract the expected BG effect of the dose from the observed BG data, resulting in a net BG response that the dose is not responsible for, and using this net response to calculate BG and BG trend corrections such that the insulin (or IOB) is not double-counted.

Safety/Validation of Trend Adjust

BG response to food (e.g., carbs) and insulin is dependent upon the individual person and can vary throughout the day, or due to other factors (e.g., exercise, pregnancy, menstrual cycle, stress, hydration, etc.) so any dose calculator must be properly set up for its particular user. While some general guidelines exist for estimating these values, typically experience and trial-and-error refinement are required to achieve accurate settings for a user. Additionally, even if correct values are known for a user, the values may be entered incorrectly into a new system or after a change in therapy.

Use of a traditional dose calculator is already susceptible to error in settings, but enabling BG trend correction may compound the effect of error. In particular, the settings for Insulin Sensitivity Factor (e.g. amount of insulin required to adjust BG) and Duration of Insulin Action (also referred to as Insulin Action Time; e.g. the rate at which insulin decays in the body, used to calculate IOB) are both critical to properly correcting for BG trends.

By way of example, methods are described herein to achieve the most accurate BG control for a user (e.g. by mitigating the risk of compounding error when adjusting the dose calculation for BG trend), where the app 40 can correct for BG and BG Trend, but only if it is safe to do so and will not cause over-correction due to poorly set parameters. By way of example, to maximize control and safety, the app 40 may implement one or more of the risk mitigation methods described below, in any combination.

In some embodiments, the app 40 may mitigate risk of compounding error when adjusting the dose calculation for BG trend by establishing a "trust" or "confidence" value for critical parameters such as Insulin Sensitivity Factor and Duration of Insulin Action. By way of example, in some implementations the app 40 may require a minimum confidence level for critical parameters before enabling BG Trend Correction, omitting it from dose calculations until this confidence level is attained. In some implementations, the app 40 may apply trend correction in a reduced proportion based on confidence, for example, applying only 50% of the trend correction value if the critical parameters have 50% confidence. In some implementations, the app 40 may initially set confidence to a low value or zero when the system is initially setup or a user changes therapy. In some implementations, the app 40 may increase confidence as the user uses the dose calculator module 75 and outcomes are favorable. In some implementations, the app 40 may decrease confidence as the user uses the dose calculator module 75 and outcomes are unfavorable. In some implementations, the app 40 may define confidence as a running average of BG response after use of the dose calculator module 75. In some implementations, the app 40 may compare the calculated BG response to the actual BG response (e.g. supplied by the CGM 60) after use of the dose calculator module 75; increasing confidence if the calculated and actual responses are within a minimum threshold, and decreasing confidence if the calculated and actual responses are beyond a maximum threshold. In some implementations, the app 40 may (i) calculate the delta between calculated (predicted) and actual BG response at a time period after use of the dose calculator module 75 and administration of a dose by the pen device 20; (ii) divide the calculated delta by a fixed error range, such as 40 mg/dL, to generate a percent error; (iii) identify the absolute value of the percent error; (iv) calculate a running average of the percent error; and (v) define the calculated running average of the percent error as Confidence, where high values indicate high error and low confidence, and vice versa. In some implementations, the app 40 may apply BG trend correction for a shorter Projection Time initially or when confidence is low.

In some embodiments, the app 40 may mitigate risk of compounding error when adjusting the dose calculation for BG trend by requiring a minimum number of uses of the dose calculator module 75 before enabling BG trend compensation. In some embodiments, the app 40 may require a minimum number of dose calculator module 75 uses and a minimum confidence value before enabling BG trend compensation. In some embodiments, the app 40 may enable BG trend compensation for downward trends (e.g., reducing insulin) but not for upward trends (e.g., increasing insulin). In some embodiments, the app 40 may apply a higher percent correction for downward trends than upward trends. (e.g., downward trend correction may be multiplied by 80%, but upward trend correction may be multiplied by 40%). In some embodiments, the app 40 may limit BG trend corrections to a maximum value, so that small corrections can be made precisely but large corrections are avoided for safety. The app 40 may increase the maximum value over time or as confidence in parameters increases. The limits may be different for upward and downward corrections. By way of example, in some implementations the maximum value may be set as a fixed number of insulin units. In some implementations, the maximum value may be set as an equivalent mg/dL so it is scaled proportionately by the user's Insulin Sensitivity Factor.

In some embodiments, the app 40 may mitigate risk of compounding error when adjusting the dose calculation for BG trend by performing a primary dose calculation to display to the user without BG trend compensation, or with reduced BG trend compensation, and concurrently perform a secondary dose calculation with BG trend compensation as a safety check against hypoglycemia. For example, if the secondary dose calculation predicts BG below a threshold (for example 80 mg/dL) then the primary dose calculation may not be displayed, and instead app 40 instructs the user to eat or to avoid taking insulin. In this way, the dose calculator module 75 functions normally without (or with reduced) BG trend compensation, but the full safety benefit of hypoglycemia prevention from BG trend compensation is realized.

In some embodiments, in addition to limiting trend correction based on confidence of Insulin Sensitivity Factor and Duration of Insulin Action, the app 40 may define confidence metrics (and/or error metrics). These confidence (and/or error) metrics may be defined in any number of ways. By way of example, there may be an overall confidence metric for the full dose calculator setup, one confidence metric for every parameter, and/or a confidence metric for every parameter at multiple times of day, meals of the day, and/or days of the week. (For example, the app 40 may assign a high confidence score to Insulin Sensitivity Factor for morning corrections but lower confidence score for evening corrections, or the app 40 may assign a low confidence score to a COB Factor for breakfast meals but higher confidence score for dinner meals.)

In some embodiments, the system 10 may update the confidence score for each parameter (e.g. Insulin Sensitivity Factor, Duration of Insulin Action, etc.) whether or not the dose calculator module 75 was used, as long as BG is monitored (e.g. by a CGM 60), insulin doses are logged (e.g. by the pen device 20 and/or app 40), and meals are logged (e.g. by the app 40). The health management app 40 may use the currently set parameters to estimate the effect on BG of meals and insulin doses, and compare the estimated effect on BG to the actual observed BG response in the user. In some embodiments, an error function may be defined by the app 40 for a time period after every dose and meal to statistically attribute error between calculated and actual BG to the various parameters. Alternatively, the system 10 may opportunistically validate parameters when they are relevant in isolation. For example, when no meal is eaten but a BG correction dose is applied, his gives a non-convoluted dataset for validating Insulin Sensitivity Factor. For example, when BG is flat at target and a meal dose is taken, this gives a non-convoluted dataset for validating COB Factor.

By way of example, consistent error (between calculated or expected BG and actual BG) in post-meal BG readings indicates low confidence in COB Factor, whereas a high degree of variability in post-meal BG error (between calculated or expected BG and actual BG) indicates low confidence in the user's estimation of grams of carbohydrate consumed.

By way of example, the app 40 may report confidence metrics directly to the user (e.g. by displaying on the display unit 36 of the companion device, or by generating a report and transmitting electronically to a user-specified location) or a physician after a determined time period of the patient user using the system 10 to indicate problems or parameters that need to be adjusted. The system 10 may also generate an alert proactively if confidence is demonstrated to be poor (e.g., error is high) to alert the user or physician of an urgent problem to correct that may lead to poor BG outcomes.

In some embodiments, confidence metrics may be used by the app 40 to omit or limit the implementation of various corrections. For example, the app 40 may limit the maximum meal size that the user is able to enter into the system while Carbohydrate (or COB) Factor has low confidence, or the app 40 may limit a maximum BG correction dose while Insulin Sensitivity Factor has low confidence to reduce the chance of over-correction.

In some embodiments, the app 40 may use confidence metrics to estimate statistical worst-case true values of calculation parameters. For example, if each calculation parameter is modeled as a bell curve representing statistical probability of any particular value, the center of the bell curve would represent the present setpoint but the width of the bell curve would represent the confidence, so low confidence would result in a wide bell-curve. Given the statistical probability that the parameters are set incorrectly, the app 40 may estimate "worst-case" parameters based on a percentile amount of the bell curve. For example, the dose calculator module 75 may be run with $25^{th}$ percentile parameter values as a safety check against the calculation performed at nominal parameter values. While the nominal calculation is the normal calculation used by the dose calculator module 75 when calculating a dose recommendation to be given to the user, the app 40 may use the "worst-case" parameters to predict the worst-case BG outcome, assuming the parameters are actually set incorrectly. If the app 40 determines that the worst-case BG outcome is unacceptably low or high, the app 40 may use the worst-case calculation to reduce the recommendation to a safer level. This would have the greatest impact when large corrections are being made for very high BG and/or very large meals, and the risk of incorrectly set parameters is high.

For example, if a user was at 300 mg/dL and about to eat a 40 carb meal, the nominal dose calculation performed by the app 40 may result in a dose recommendation of 12 units of insulin, but the worst-case calculation predicts that 12 U could drive the user's BG level as low as 20 mg/dL, the app 40 may reduce the dose recommendation to 8 U, for which the worst-case calculation predicts would not drive the user below 50 mg/dL even if calculation parameters are incorrect as statistically estimated.

Conservative Mode

In some embodiments in accordance with the present technology, the disclosed systems and methods may be equipped with a "conservative mode" or a variable parameter of conservatism for a patient user. By way of example, this may be used in cases where insulin parameters are not yet established or trusted (such as for a new user), cases where a user has just changed therapy and is monitoring their body's response, cases where a user may be new to carb counting and prone to mis-estimation, or high-risk cases where hypoglycemia safety is more critical than tight BG control, such as for children, ill patients, or elderly patients.

As described above, the effects of an incorrect insulin sensitivity factor can be amplified by adjusting for BG value and trend. For example, in the case of a user with a high BG and a high increasing rate of change, a dose calculator will likely recommend insulin for both, and an incorrectly high insulin sensitivity factor will cause both factors to be too high, resulting in substantially too high of a dose recommendation. For this reason, the health management app 40 may reduce the trend adjustment factor by a fixed offset and/or percentage (e.g., whichever is greater). For example, the app 40 may decrease trend adjustments by 1 U or 50%, whichever is greater, with a floor value of zero (e.g., a 0.5 U adjustment would be reduced to 0 U, not −0.5 U.)

In some embodiments, to focus on hypoglycemia protection, the app 40 may apply reductions in trend adjustment to upward trends (e.g., when increased insulin would be recommended) and less or not at all to downward trends (e.g., when decreased insulin would be recommended).

In some embodiments, the app 40 may cap trend adjustments at a maximum value so that small adjustments can be made precisely, but large adjustments have reduced potential for over-correction.

In some embodiments, the app 40 may increase target BG to provide a safety buffer against hypoglycemia. This may be applied at all times, or only in extreme cases of very large corrections, such as with an extreme high or low BG (e.g. as measured by the CGM 60), a high rate of change (e.g. as detected by the CGM 60), or a large meal consumed by the user. The increased target BG may be based on one of these factors or the total net insulin calculation.

By way of example, in cases of a large dose calculation, such as with high and rapidly increasing BG, a portion of the calculated dose recommendation may be split into multiple doses, for example an initial dose administered at the time of the dose recommendation and a follow-up dose administered after a period of time (e.g. 1 hour) has elapsed after administration of the initial dose. The dose may be capped at a maximum value, or split by percentage (e.g., 60% of the dose administered initially, 40% to be taken later). At the future time point (e.g. the time of the administration of the follow-up dose) the BG response can be monitored (e.g. by the CGM 60) and the app 40 may run the dose calculation again with the benefit of the true measured BG and BG rate of change at this future time, and display a dose recommendation for the follow-up dose, helping to prevent overcorrection by the initial dose.

In some embodiments, once a patient is established with the intelligent medicine administering system 10 (e.g. including the health management app 40 with dose calculator module 75), and the app 40 has had time to refine and confirm the user's clinical settings over time (e.g., by "learning" from the user's use behavior, by manual adjustment by the user, and/or by manual adjustment by the user's physician, BG and BG rate of change (trend) is objectively measured by a sensor (e.g. CGM) 60 and communicated to the app 40, and IOB is calculated by the app 40 from objective insulin dose records. Thus, the largest source of uncertainty in the dose calculation after a period of sustained use by the user is likely to be the user's meal size estimates, or estimated grams of carbohydrate in a meal. For this reason, the app 40 may include a conservative mode that enables full BG and trend correction, but applies safeguards against the carb covering portion of the dose recommendation (R) calculation. By way of example, the app 40 may use a nonlinear carbohydrate factor that applies full carb correction up to a certain estimated meal size, but above that the nonlinear carb factor only applies a portion of the full calculation of insulin required. For example, if a user has a carb factor of 5 grams/unit and enters a 50 gram meal, the dose calculator module 75 of the app 40 may only apply the 5 gram/unit factor to the first 30 grams, and an increased carb factor such as 10 grams/unit to the remainder of the meal. So mathematically, in the absence of the nonlinear carb factor, the dose calculator module 75 would normally recommend 50/5=10 U of insulin. In contrast, to safeguard against overestimation of carbs in the consumed food and thus over-correction with insulin, the recommended dose calculation with the nonlinear carb factor applied would be (30/5)+(20/10)=8 U of insulin. In some embodiments, by way of example, for a meal over a particular size (e.g. 30 grams of carbohydrate), the app 40 may limit the grams of carbs or the calculated insulin correction for carbs at a set maximum threshold, and prompt the user to perform a follow-up BG check and dose calculation at some time in the future after monitoring the effect of the initial dose.

Exercise Mode

Exercise is known to lower a patient's BG. This can cause a risk of hypoglycemia during exercise, and often prompts patients to elevate their BG prior to beginning exercise, both as a safety margin against hyperglycemia and in anticipation of BG dropping once the exercise begins.

In some embodiments in accordance with the present technology, the dose calculator module 75 of the app 40 may include an "exercise mode" that adjusts calculations to help a patient user maintain stable and safe BG during exercise. The exercise mode may be activated and/or deactivated by any of a number of suitable methods. For example, in some embodiments, the app 40 may offer the user a toggle switch on the user interface that when toggled allows the user to enable or disable exercise mode manually. In some embodiments, once toggled, exercise mode may remain enabled for subsequent dose calculations until toggled off again, and/or the app 40 may revert back to non-exercise-mode after a set amount of time has elapsed, for example 8 hours. In some embodiments, the exercise mode may be activated and/or deactivated based upon location information (e.g. supplied to the app 40 by a GPS module of the user's companion device 30) indicating the user is at a gym or other place where exercise frequently occurs, or a place in which the user normally visits with the purpose of exercising (e.g. park, beach, trail, etc.). In some embodiments, the exercise mode may be activated and/or deactivated based upon location information indicating that the user is at a location in which the user normally visits or has previously visited with the purpose of exercising (e.g. park, beach, trail, etc.). In some embodiments, the exercise mode may be activated and/or deactivated based on location tracking indicating the user is traveling at a common running or cycling speed, which would imply the user is engaging in one of those activities. In some embodiments, the exercise mode may be activated and/or deactivated based upon scheduled events in the user's calendar on the user's companion device 30 (and the app 40 has been given permission to access the user's digital calendar) that indicate exercise. In some embodiments, the exercise mode may be activated and/or deactivated based on output from an accelerometer or fitness tracker that detects exercise such as running, walking, cycling, training, or other sports. In some embodiments, the exercise mode may be activated and/or deactivated based upon output from a heart rate monitor or other connected sensor detecting physiological signs of exercise such as elevated heartrate or increased perspiration. In some embodiments, the exercise mode may be activated and/or deactivated based on a sudden drop in BG not associated with insulin or other logged events. In some embodiments, any of the triggers listed above may also be used to set or detect the type or intensity of exercise, allowing variable application of exercise mode. Thus, rather than simply being on or off, the app 40 may apply the exercise mode proportionately based on the exercise that the user is engaged in.

By way of example, when the exercise mode is enabled, the health management app 40 may perform one or more functions designed to monitor the user's BG response to the exercise, alert the user to BG issues that may arise during the exercise, and/or adjust subsequent insulin dose recommendations to account for the observed BG response. For example, in some embodiments, when exercise mode is enabled, the app 40 may set a higher BG target as pre-configured by the user or user's physician. In some embodiments, when exercise mode is enabled, the app 40 may set a higher BG target as a pre-set offset from normal target BG. In some embodiments, when exercise mode is enabled, the app 40 may alert the user if their present (pre-exercise) BG is below a minimum safe threshold, indicating that the user should consume carbs to elevate BG prior to beginning exercise to minimize risk of hypoglycemia. In some embodiments, when exercise mode is enabled, the app 40 may more aggressively warn the user of a low BG and/or downward BG trend during exercise, using a higher alert threshold than during non-exercise. In some embodiments, when exercise mode is enabled, the app 40 may adjust insulin sensitivity factor and/or carbohydrate factor to values set for exercise, which may differ from the appropriate non-exercise value. In some embodiments, when exercise mode is enabled, the app 40 may adjust the insulin action time, reflecting faster bumdown of insulin in the body to more accurately calculate IOB and more accurately model expected BG rate of change.

In some embodiments, the system 10 may model the impact of exercise on glucose for the user including the effects of a particular type or intensity of exercise. By way of example, when the app 40 is in exercise mode, the system 10 first detects that exercise is occurring, e.g. based on the user manually reporting the start of an exercise workout (e.g. through a user interface on the companion device 30) or by peripheral sensors worn by the user in communication with the app 40 indicating a physiological change (e.g., a heart rate increase or muscle movement) consistent with exercise. In some embodiments, the user may indicate to the app 40 an exercise plan, including (by way of example) type, intensity, and/or duration of planned exercise, or the app 40 may automatically detect the type, intensity, and/or duration of the exercise based on sensor data and/or past exercise history of the user. The app 40 (e.g. by way of a CGM 60) may then monitor and record BG response during the exercise activity. The app 40 may assess success of past exercise mode usage, retroactively model what would have been the correct dose compensation to administer prior to the planned exercise activity or how much carbohydrate the user may need to consume immediately after the completed exercise activity, and/or incrementally adjust dose calculation parameters over time as the app 40 gauges the success of each use. In addition to dose calculator adjustments, safety mitigations such as hypoglycemia alert thresholds may be calibrated per user and per type of exercise. For these exercise assessments, the app 40 may normalize for recent insulin administered, recent food intake, un-optimized basal rate and/or missed basal dose as set forth above.

Finger stick or CGM Scan Optimization

Some glucose monitoring systems are continuously connected to a user interface (such as a smart phone app), but other systems require manually scanning a sensor to upload data or manually taking a finger stick reading to check BG. In these systems, the user may infrequently update BG, may forget to do so, may fail to check BG after a major correction or concerning BG trend, or may fail to check before making an important dosing decision. Some systems exist that function as fixed daily reminders to test BG, but a more intelligent and adaptable solution would deliver a more optimal result.

In some embodiments of the intelligent medicine administering system 10 of the present disclosure, the sensor device 60 may comprise a wearable continuous glucose monitor that is not configured to automatically transmit BG data to the health management app 40, or in some instances the user may not use a CGM at all, in which case the sensor device 60 may comprise a BG meter. In such instances, the health management app 40 may periodically prompt the user for a BG check. For example, one way in which a user of a finger stick device may perform a BG check once prompted is to use a finger stick device to obtain a blood sample, insert the blood sample into the BG meter, and view the BG data on a display unit of the BG meter. The BG data may then be transferred manually by the user to the system 10, for example by entering the BG data on the user interface of the companion device 30, or transmitted via wireless communication between the BG meter (if capable of wireless communication) and the companion device 30. By way of example, such wireless communication may be achieved by any suitable wireless communication technology, including but not limited to Bluetooth, Bluetooth low energy, NFC, WiFi, cellular, and the like. By way of example, when prompted by the app 40 for a BG check, a user of a wearable CGM device that is not in continuous wireless communication with the companion device 30 but is equipped with NFC connectivity may scan a sensor on the CGM device with either their companion device 30 or a reader device that then transfers the BG data to the companion device wirelessly.

For example, in some embodiments, the app 40 may prompt the user to perform a BG check prior to using (or activating) the dose calculator module 75 of the health management app 40. In some embodiments, the app 40 may prompt the user to perform a BG check upon user interaction with the dose calculator module 75 but before acting on a recommendation (e.g. by administering a dose with the pen device 20) so that BG correction can be included.

In some embodiments, the app 40 may prompt the user to perform a BG check upon expiration of a fixed time period after a large (e.g. above a defined threshold) insulin dose to check for a correct response. In some embodiments, the app 40 may prompt the user to perform a BG check upon expiration of a fixed time period after a large (e.g. above a defined threshold) meal correction. This is because regardless of the total insulin taken, if the meal portion of the dose calculation is large, it may contain large error, so following-up on BG is an important safety precaution. In some embodiments, the app 40 may prompt the user to perform a BG check upon expiration of a fixed time period after a large (e.g. above a defined threshold) BG trend correction. This is because regardless of the total insulin taken, if the BG trend portion of the dose calculation is large it may contain large error, so following-up on BG is an important safety precaution. In some embodiments, the app 40 may prompt the user to perform a BG check at a time when the user is forecasted to exceed a minimum or maximum BG threshold based on past BG level and rate of change. In some embodiments, the app 40 may prompt the user to perform a BG check at a time of day (and/or day of the week) when the user has previously shown a pattern of poor glycemic control, allowing the user to identify a risk in real-time and giving the opportunity to proactively counteract it with a dose of insulin or food intake.

By way of example, a continuous glucose monitor that requires manual updating may sync all past data with the app 40. Once synchronized, there are no gaps in data, and the full 24 hr/day BG trend can be viewed and analyzed by the app 40. However, for discrete finger stick BG meters the only BG data points are those collected when the user has drawn blood and measured their glucose. In addition to the methods described above, there are additional ways that finger stick BG meters can be optimized via interaction with the health management app 40 so the user can take the minimal number of finger sticks with the maximum benefit. For example, in some embodiments the user may input their preferred or maximum number of finger sticks per day into the health management app 40 by way of the user interface of the user's companion device 30. While many more finger stick events may be optimal for glycemic control, if the user refuses or is unable to take more, the system 10 may prompt the user to execute those finger sticks at the most optimal times. In some embodiments, the app 40 may initially prioritize the most safety-critical times to check BG, e.g., before bed or after a large insulin dose. Then, once overnight BG is demonstrated stable and dose calculation parameters have high confidence even with larger insulin doses, finger stick BG measurements may be taken at other times to better optimize and/or troubleshoot BG issues at other times, e.g., after breakfast, etc. In some embodiments, the app 40 may initially prioritize optimization of basal insulin, prompting the user to check BG during periods of fasting, or for example when going to bed and after waking up in the morning. In some embodiments, the app 40 may prompt the user for a follow-up BG measurement after a new type of food or a new meal size is eaten, both to confirm safety after the meal is taken and to verify that the parameters used in the dose recommendation calculation are accurate. Whereas when the user is repeating a common scenario with a common food, the BG outcome may be more predictable, and a follow-up finger stick is less necessary. In some embodiments, the app 40 may systematically recommend finger stick BG readings at staggered times throughout the day, after a meal, after a dose, and/or after other events such as exercise or waking up. In this way, even though each day may only have a small number of BG values, aggregated over time (for example, 3 months between physician visits) the app 40 can use these values to generate an averaged snapshot of BG control throughout the day, similar to what CGM users are able to achieve by overlapping or averaging datasets across multiple days. For example, with just one additional finger stick BG reading during waking hours of the day (e.g., 18 hours) at a different hour each day, after three months there would be at least 5 BG values per hour of the day that could be plotted or analyzed to show trends of glycemic control that cannot be seen from an individual finger stick on a single day.

EXAMPLES

Further to the description of the embodiments of the present technology described above, the present technology includes the following embodiments, by way of example.

Embodiment 1 includes a method for determining a recommended dose of insulin to administer to a patient user of an insulin delivery device using a dose calculator, comprising: determining a plurality of dose calculator parameters for the patient user, including a blood glucose correction parameter, a carbohydrates cover parameter, an insulin on board (IOB) parameter, a glucose trend adjustment parameter, and a carbohydrates on board (COB) adjustment parameter for the patient user, wherein the COB adjustment parameter includes a quotient of an estimated value for unmetabolized carbohydrates ingested from recent meals by the patient user and an insulin-to-carbohydrates ratio of the patient user; and producing an insulin dose recommendation based on an estimated sum of the blood glucose correction parameter, the glucose trend adjustment parameter, the carbohydrates cover parameter and the COB adjustment parameter subtracted by the IOB parameter.

Embodiment 2 includes the method of embodiment 1 or any of embodiments 3 through 22, wherein the estimated value for unmetabolized carbohydrates of the COB adjustment parameter includes a carbohydrates burndown parameter.

Embodiment 3 includes the method of embodiments 1 or 2 or any of embodiments 4 through 22, wherein the carbohydrates burndown parameter comprises a fixed time period after a last ingested meal by the patient user during which carbohydrates are typically expected to be metabolized.

Embodiment 4 includes the method of any of embodiments 1 through 3 or any of embodiments 5 through 22, wherein the carbohydrates bumdown parameter includes a variable value associated with a metabolism rate of specific carbohydrates.

Embodiment 5 includes the method of any of embodiments 1 through 4 or any of embodiments 6 through 22, wherein the carbohydrates bumdown parameter includes a qualitative value associated with at least one of a fast burndown rate and a slow burndown rate.

Embodiment 6 includes the method of any of embodiments 1 through 5 or any of embodiments 7 through 22, wherein the carbohydrates bumdown parameter includes an estimated value based on a population data for a particular type of food.

Embodiment 7 includes the method of any of embodiments 1 through 6 or any of embodiments 8 through 22, wherein the carbohydrates burndown parameter is determined by: assigning the carbohydrates burndown parameter a value corresponding to a first predetermined burndown rate associated with a fast metabolic rate of carbohydrate for a first portion of a time period after a last ingested meal by the patient user; and assigning the carbohydrates burndown parameter a value corresponding to a second predetermined burndown rate associated with a slow metabolic rate of carbohydrate for a second portion of the time period.

Embodiment 8 includes the method of any of embodiments 1 through 7 or any of embodiments 9 through 22, wherein the carbohydrates burndown parameter is determined by: assigning the carbohydrates burndown parameter a value corresponding to a first predetermined burndown rate associated with a fast metabolic rate of carbohydrate for a first portion of a time period after a last ingested meal by the patient user; and assigning the carbohydrates burndown parameter a value corresponding to a second burndown rate, wherein the second burndown rate is determined based on a net carbohydrates response estimation using an initial blood glucose value, a rate of change of the blood glucose levels over the a portion of the time period, and a current blood glucose value of the patient user.

Embodiment 9 includes the method of any of embodiments 1 through 8 or any of embodiments 10 through 22, wherein the blood glucose correction parameter includes a difference value between a current glucose level of the patient user and a quotient of a target glucose level and a sensitivity factor of the patient user.

Embodiment 10 includes the method of any of embodiments 1 through 9 or any of embodiments 11 through 22, wherein the carbohydrates cover parameter includes a quotient of a carbohydrates value and the insulin-to-carbohydrates ratio of the patient user.

Embodiment 11 includes the method of any of embodiments 1 through 10 or any of embodiments 12 through 22, wherein the IOB parameter includes an estimated value of remaining units of insulin in the patient user's body.

Embodiment 12 includes the method of any of embodiments 1 through 11 or any of embodiments 13 through 22, wherein the glucose trend adjustment parameter comprises an estimated value of a rate of change in glucose levels of the patient multiplied by a projection time and then divided by an insulin sensitivity factor (ISF) of the patient user.

Embodiment 13 includes the method of any of embodiments 1 through 12 or any of embodiments 14 through 22, further comprising: determining a confidence value for each of the dose calculator parameters.

Embodiment 14 includes the method of any of embodiments 1 through 13 or any of embodiments 15 through 22, wherein the glucose trend adjustment parameter is disabled upon determination that at least one of the determined confidence values is below a respective predetermined threshold confidence value.

Embodiment 15 includes the method of any of embodiments 1 through 14 or any of embodiments 16 through 22, wherein the glucose trend adjustment parameter is scaled proportionally to at least one of the determined confidence values.

Embodiment 16 includes the method of any of embodiments 1 through 15 or any of embodiments 17 through 22, wherein the glucose trend adjustment parameter includes a maximum value corresponding to at least one of the determined confidence values.

Embodiment 17 includes the method of any of embodiments 1 through 16 or any of embodiments 18 through 22, further comprising: displaying the produced insulin dose recommendation on at least one of a display unit of the insulin delivery device and a display unit of a mobile device in wireless communication with the insulin delivery device.

Embodiment 18 includes the method of any of embodiments 1 through 17 or any of embodiments 19 through 22, wherein the mobile device is implemented on one or more of a smartphone, a tablet, a smartwatch, a smartglasses, a wearable device, or a laptop or a desktop computer.

Embodiment 19 includes the method of any of embodiments 1 through 18 or any of embodiments 20 through 22, wherein at least one of the IOB parameter and the COB adjustment parameter comprises a projected future value.

Embodiment 20 includes the method of any of embodiments 1 through 19 or any of embodiments 21 through 22, wherein the glucose trend adjustment parameter is enabled for downward trends and disabled for upward trends.

Embodiment 21 includes the method of any of embodiments 1 through 20 or embodiment 22, wherein the glucose trend adjustment parameter is enabled for downward trends and upward trends to a predetermined threshold value.

Embodiment 22 includes the method of any of embodiments 1 through 21, wherein the glucose trend adjustment parameter is enabled for downward trends and enabled for upward trends, and a scaling factor is applied to upward trends.

Embodiment 23 includes a computer-implemented method for determining an insulin dose recommendation on a computing device comprising a processor and a memory, the method comprising: determining, at the processor, a blood glucose correction calculation parameter for a patient user of an insulin delivery device; determining, at the processor, a carbohydrates cover calculation parameter for the patient user; determining, at the processor, an insulin on board (IOB) calculation parameter for the patient user; determining, at the processor, a glucose trend adjustment calculation parameter for the patient user; determining, at the processor, a carbohydrates on board (COB) adjustment calculation parameter for the patient user, wherein the COB adjustment parameter includes a quotient of an estimated value for unmetabolized carbohydrates ingested from recent meals by the patient user and an insulin-to-carbohydrates ratio of the patient user; and producing, at the processor, an insulin dose recommendation based on an estimated sum of the blood glucose correction parameter, the glucose trend adjustment parameter, the carbohydrates cover parameter and the COB adjustment parameter subtracted by the IOB parameter.

Embodiment 24 includes the computer-implemented method of embodiment 23 or any of embodiments 25 through 44, wherein the estimated value for unmetabolized carbohydrates of the COB adjustment parameter includes a carbohydrates burndown parameter.

Embodiment 25 includes the computer-implemented method of embodiments 23 or 24 or any of embodiments 26 through 44, wherein the carbohydrates burndown parameter comprises a fixed time period after a last ingested meal by the patient user during which carbohydrates are typically expected to be metabolized.

Embodiment 26 includes the computer-implemented method of any of embodiments 23 through 25 or any of embodiments 27 through 44, wherein the carbohydrates burndown parameter includes a variable value associated with a metabolism rate of specific carbohydrates.

Embodiment 27 includes the computer-implemented method of any of embodiments 23 through 26 or any of embodiments 28 through 44, wherein the carbohydrates burndown parameter includes a qualitative value associated with at least one of a fast burndown rate and a slow burndown rate.

Embodiment 28 includes the computer-implemented method of any of embodiments 23 through 27 or any of embodiments 29 through 44, wherein the carbohydrates burndown parameter includes an estimated value based on a population data for a particular type of food.

Embodiment 29 includes the computer-implemented method of any of embodiments 23 through 28 or any of embodiments 30 through 44, wherein the carbohydrates burndown parameter is determined by: assigning the carbohydrates burndown parameter a value corresponding to a first predetermined burndown rate associated with a fast metabolic rate of carbohydrate for a first portion of a time period after a last ingested meal by the patient user; and assigning the carbohydrates burndown parameter a value corresponding to a second predetermined burndown rate associated with a slow metabolic rate of carbohydrate for a second portion of the time period.

Embodiment 30 includes the computer-implemented method of any of embodiments 23 through 29 or any of embodiments 31 through 44, wherein the carbohydrates burndown parameter is determined by: assigning the carbohydrates burndown parameter a value corresponding to a first predetermined burndown rate associated with a fast metabolic rate of carbohydrate for a first portion of a time period after a last ingested meal by the patient user; and assigning the carbohydrates bumdown parameter a value corresponding to a second burndown rate, wherein the second burndown rate is determined based on a net carbohydrates response estimation using an initial blood glucose value, a rate of change of the blood glucose levels over the a portion of the time period, and a current blood glucose value of the patient user.

Embodiment 31 includes the computer-implemented method of any of embodiments 23 through 30 or any of embodiments 32 through 44, wherein the blood glucose correction parameter includes a difference value between a current glucose level of the patient user and a quotient of a target glucose level and a sensitivity factor of the patient user.

Embodiment 32 includes the computer-implemented method of any of embodiments 23 through 31 or any of embodiments 33 through 44, wherein the carbohydrates cover parameter includes a quotient of a carbohydrates value and the insulin-to-carbohydrates ratio of the patient user.

Embodiment 33 includes the computer-implemented method of any of embodiments 23 through 32 or any of embodiments 34 through 44, wherein the IOB parameter includes an estimated value of remaining units of insulin in the patient user's body.

Embodiment 34 includes the computer-implemented method of any of embodiments 23 through 33 or any of embodiments 35 through 44, wherein the glucose trend adjustment parameter comprises an estimated value of a rate of change in glucose levels of the patient multiplied by a projection time and then divided by an insulin sensitivity factor (ISF) of the patient user.

Embodiment 35 includes the computer-implemented method of any of embodiments 23 through 34 or any of embodiments 36 through 44, further comprising: determining a confidence value for each of the calculation parameters.

Embodiment 36 includes the computer-implemented method of any of embodiments 23 through 35 or any of embodiments 37 through 44, wherein the glucose trend adjustment parameter is disabled upon determination that at least one of the determined confidence values is below a respective predetermined threshold confidence value.

Embodiment 37 includes the computer-implemented method of any of embodiments 23 through 36 or any of embodiments 38 through 44, wherein the glucose trend adjustment parameter is scaled proportionally to at least one of the determined confidence values.

Embodiment 38 includes the computer-implemented method of any of embodiments 23 through 37 or any of embodiments 39 through 44, wherein the glucose trend adjustment parameter includes a maximum value corresponding to at least one of the determined confidence values.

Embodiment 39 includes the computer-implemented method of any of embodiments 23 through 38 or any of embodiments 40 through 44, further comprising: displaying the produced insulin dose recommendation on at least one of a display unit of the insulin delivery device and a display unit of a mobile device in wireless communication with the insulin delivery device.

Embodiment 40 includes the computer-implemented method of any of embodiments 23 through 39 or any of embodiments 41 through 44, wherein the mobile device is implemented on one or more of a smartphone, a tablet, a smartwatch, a smartglasses, a wearable device, or a laptop or a desktop computer.

Embodiment 41 includes the computer-implemented method of any of embodiments 23 through 40 or any of embodiments 42 through 44, wherein at least one of the IOB parameter and the COB adjustment parameter comprises a projected future value.

Embodiment 42 includes the computer-implemented method of any of embodiments 23 through 41 or any of embodiments 43 or 44, wherein the glucose trend adjustment parameter is enabled for downward trends and disabled for upward trends.

Embodiment 43 includes the computer-implemented method of any of embodiments 23 through 42 or embodiment 44, wherein the glucose trend adjustment parameter is enabled for downward trends and upward trends to a predetermined threshold value.

Embodiment 44 includes the computer-implemented method of any of embodiments 23 through 43, wherein the glucose trend adjustment parameter is enabled for downward trends and enabled for upward trends, and a scaling factor is applied to upward trends.

Embodiment 45 includes a computer program product installable on a mobile communication device and configured for use with a peripheral electronic medical device in wireless communication with the mobile communication device, the computer program product embodied in a non-transitory computer readable storage medium and comprising computer instructions for: determining a blood glucose correction calculation parameter for the patient user; determining a carbohydrates cover calculation parameter for the patient user; determining an insulin on board (IOB) calculation parameter for the patient user; determining a glucose trend adjustment calculation parameter for the patient user; determining a carbohydrates on board (COB) adjustment calculation parameter for the patient user, wherein the COB adjustment parameter includes a quotient of an estimated value for unmetabolized carbohydrates ingested from recent meals by the patient user and an insulin-to-carbohydrates ratio of the patient user; and producing an insulin dose recommendation based on an estimated sum of the blood glucose correction parameter, the glucose trend adjustment parameter, the carbohydrates cover parameter and the COB adjustment parameter subtracted by the IOB parameter.

Embodiment 46 includes the computer program product of embodiment 45 or any of embodiments 47 through 67, wherein the estimated value for unmetabolized carbohydrates of the COB adjustment parameter includes a carbohydrates burndown parameter.

Embodiment 47 includes the computer program product of embodiments 45 or 46 or any of embodiments 48 through 67, wherein the carbohydrates burndown parameter comprises a fixed time period after a last ingested meal by the patient user during which carbohydrates are typically expected to be metabolized.

Embodiment 48 includes the computer program product of any of embodiments 45 through 47 or any of embodiments 49 through 67, wherein the carbohydrates burndown parameter includes a variable value associated with a metabolism rate of specific carbohydrates.

Embodiment 49 includes the computer program product of any of embodiments 45 through 48 or any of embodiments 50 through 67, wherein the carbohydrates burndown parameter includes a qualitative value associated with at least one of a fast burndown rate and a slow burndown rate.

Embodiment 50 includes the computer program product of any of embodiments 45 through 49 or any of embodiments 51 through 67, wherein the carbohydrates burndown parameter includes an estimated value based on a population data for a particular type of food.

Embodiment 51 includes the computer program product of any of embodiments 45 through 50 or any of embodiments 52 through 67, further comprising computer instructions for determining the carbohydrates burndown parameter by: assigning the carbohydrates burndown parameter a value corresponding to a first predetermined burndown rate associated with a fast metabolic rate of carbohydrate for a first portion of a time period after a last ingested meal by the patient user; and assigning the carbohydrates burndown parameter a value corresponding to a second predetermined burndown rate associated with a slow metabolic rate of carbohydrate for a second portion of the time period.

Embodiment 52 includes the computer program product of any of embodiments 45 through 51 or any of embodiments 53 through 67, further comprising computer instructions for determining the carbohydrates burndown parameter by: assigning the carbohydrates burndown parameter a value corresponding to a first predetermined burndown rate associated with a fast metabolic rate of carbohydrate for a first portion of a time period after a last ingested meal by the patient user; and assigning the carbohydrates burndown parameter a value corresponding to a second burndown rate, wherein the second burndown rate is determined based on a net carbohydrates response estimation using an initial blood glucose value, a rate of change of the blood glucose levels over the a portion of the time period, and a current blood glucose value of the patient user.

Embodiment 53 includes the computer program product of any of embodiments 45 through 52 or any of embodiments 54 through 67, wherein the blood glucose correction parameter includes a difference value between a current glucose level of the patient user and a quotient of a target glucose level and a sensitivity factor of the patient user.

Embodiment 54 includes the computer program product of any of embodiments 45 through 53 or any of embodiments 55 through 67, wherein the carbohydrates cover parameter includes a quotient of a carbohydrates value and the insulin-to-carbohydrates ratio of the patient user.

Embodiment 55 includes the computer program product of and of embodiments 45 through 54 or any of embodiments 56 through 67, wherein the IOB parameter includes an estimated value of remaining units of insulin in the patient user's body.

Embodiment 56 includes the computer program product of any of embodiments 45 through 55 or any of embodiments 57 through 67, wherein the glucose trend adjustment parameter comprises an estimated value of a rate of change in glucose levels of the patient multiplied by a projection time and then divided by an insulin sensitivity factor (ISF) of the patient user.

Embodiment 57 includes the computer program product of any of embodiments 45 through 56 or any of embodiments 58 through 67, further comprising: determining a confidence value for each of the calculation parameters.

Embodiment 58 includes the computer program product of any of embodiments 45 through 57 or any of embodiments 59 through 67, wherein the glucose trend adjustment parameter is disabled upon determination that at least one of the determined confidence values is below a respective predetermined threshold confidence value.

Embodiment 59 includes the computer program product of any of embodiments 45 through 58 or any of embodiments 60 through 67, wherein the glucose trend adjustment parameter is scaled proportionally to at least one of the determined confidence values.

Embodiment 60 includes the computer program product of any of embodiments 45 through 59 or any of embodiments 61 through 67, wherein the glucose trend adjustment parameter includes a maximum value corresponding to at least one of the determined confidence values.

Embodiment 61 includes the computer program product of any of embodiments 45 through 60 or any of embodiments 62 through 67, wherein at least one of the IOB parameter and the COB adjustment parameter comprises a projected future value.

Embodiment 62 includes the computer program product of any of embodiments 45 through 61 or any of embodiments 63 through 67, wherein the glucose trend adjustment parameter is enabled for downward trends and disabled for upward trends.

Embodiment 63 includes the computer program product of any of embodiments 45 through 62 or any of embodiments 64 through 67, wherein the glucose trend adjustment parameter is enabled for downward trends and upward trends to a predetermined threshold value.

Embodiment 64 includes the computer program product of any of embodiments 45 through 63 or any of embodiments 65 through 67, wherein the glucose trend adjustment parameter is enabled for downward trends and enabled for upward trends, and a scaling factor is applied to upward trends.

Embodiment 65 includes the computer program product of any of embodiments 45 through 64 or any of embodiments 66 or 67, further comprising computer instructions for: displaying the produced insulin dose recommendation on at least one of a display unit on the peripheral medical device and a display unit on the mobile communication device.

Embodiment 66 includes the computer program product of any of embodiments 45 through 65 or embodiment 67, wherein the mobile communication device comprises at least one of a smartphone, a tablet, a smartwatch, a smartglasses, a wearable device, a laptop computer, and a desktop computer.

Embodiment 67 includes the computer program product of any of embodiments 45 through 66, wherein the peripheral medical device comprises an insulin delivery device.

Embodiment 68 includes a computer program product installable on a mobile computing device and configured for use with a peripheral blood glucose monitor, the computer program product embodied in a non-transitory computer readable storage medium and comprising computer instructions for: periodically prompting a user to manually collect the user's blood glucose data and transfer the collected blood glucose data from the peripheral blood glucose monitor to the mobile computing device; and receiving the transferred data from the peripheral blood glucose monitor; wherein the mobile computing device comprises a dose calculator; and wherein the peripheral blood glucose monitor comprises at least one of a wearable continuous glucose monitor and a finger stick meter.

Embodiment 69 includes the computer program product of embodiment 68 or any of embodiments 70 through 79, wherein periodically prompting comprises prompting the user to check blood glucose data after a period of time has elapsed since the user administered a dose that included a blood glucose trend correction value exceeding a predetermined size threshold.

Embodiment 70 includes the computer program product of embodiments 68 or 69 or any of embodiments 71 through 79, wherein periodically prompting comprises prompting the user to check blood glucose data at a time when the user is forecasted to meet a minimum or maximum insulin level after at least one of a meal, dose, and exercise event.

Embodiment 71 includes the computer program product of any of embodiments 68 through 70 or any of embodiments 72 through 79, wherein periodically prompting comprises prompting the user to check blood glucose data at a time when the user has previously exhibited a pattern of poor glycemic control.

Embodiment 72 includes the computer program product of any of embodiments 68 through 71 or any of embodiments 73 through 79, wherein periodically prompting comprises prompting the user to check blood glucose data at variable times throughout a set time period, and wherein the set time period comprises at least one of a day and a week.

Embodiment 73 includes the computer program product of any of embodiments 68 through 72 or any of embodiments 74 through 79, comprising further computer instructions for: aggregating the blood glucose data collected within a defined aggregation period; arranging the aggregated data by time stamp value without regard to date collected so that the aggregated data is arranged within a single twenty-four hour period; and generating an averaged snapshot report of the user's blood glucose control throughout a day during the aggregation period.

Embodiment 74 includes the computer program product of any of embodiments 68 through 73 or any of embodiments 75 through 79, wherein the aggregation period comprises at least one of one week, one month, and three months.

Embodiment 75 includes the computer program product of any of embodiments 68 through 74 or any of embodiments 76 through 79, comprising further computer instructions for: enabling a user to select a preferred maximum number of prompts per day; and determining the appropriate times to provide the prompt based upon the user's selection.

Embodiment 76 includes the computer program product of any of embodiments 68 through 75 or any of embodiments 77 through 79, wherein determining the appropriate time to provide a prompt comprises prioritizing safety-critical times to check for blood glucose control, including at least one of before a sleep period, before a fasting period, and after administration of a large insulin dose.

Embodiment 77 includes the computer program product of any of embodiments 68 through 76 or any of embodiments 78 or 79, wherein determining the appropriate time to provide a prompt comprises prioritizing basal assessment times, including at least one of before a fasting period, before a sleep period, after a fasting period, and after a sleep period.

Embodiment 78 includes the computer program product of any of embodiments 68 through 77 or embodiment 79, wherein periodically prompting comprises prompting the user to check blood glucose data after at least one of consuming a new type of food, consuming a new meal size, and engaging in a new activity.

Embodiment 79 includes the computer program product of any of embodiments 68 through 78, wherein transferring the collected blood glucose data from the peripheral blood glucose monitor to the mobile computing device comprises at least one of: manually entering a blood glucose data value displayed on a finger stick meter into a user interface on the mobile computing device; establishing a wireless communication connection between the mobile computing device and the finger stick meter; and transferring the collected blood glucose data by way of the established wireless communication connection; and scanning a sensor on the wearable continuous glucose monitor.

Embodiment 80 includes a computer program product installable on a mobile communication device and configured for use with a peripheral electronic medical device in wireless communication with the mobile communication device, the computer program product embodied in a non-transitory computer readable storage medium and comprising a dose calculator module including computer instructions for: analyzing blood glucose data to establish dose calculator module parameters; calculating an insulin dose recommendation based upon the analyzed blood glucose data and established dose calculator parameters; and activating an exercise mode wherein at least one dose calculator parameter is adjusted to enable a patient user to maintain a blood glucose level within a target range during exercise.

Embodiment 81 includes the computer program product of embodiment 80 or any of embodiments 82 through 89, comprising further computer instructions for at least one of: increasing a target blood glucose parameter; raising a hypoglycemia alert level; adjusting an insulin sensitivity factor; adjusting an insulin to carbohydrate ratio parameter; adjusting a duration of insulin action parameter; and recommending consumption of carbohydrates to achieve a pre-exercise target blood glucose level.

Embodiment 82 includes the computer program product of embodiments 80 or 81 or any of embodiments 83 through 89, comprising further computer instructions for activating the exercise mode in response to receiving user input instructions.

Embodiment 83 includes the computer program product of any of embodiments 80 through 82 or any of embodiments 84 through 89, comprising further computer instructions for one of automatically activating the exercise mode and prompting the user to manually activate the exercise mode in response to receiving data from a user-wearable fitness tracking device.

Embodiment 84 includes the computer program product of any of embodiments 80 through 83 or any of embodiments 85 through 89, wherein the fitness tracking device comprises at least one of an accelerometer, pedometer, activity monitor, and a heart rate monitor.

Embodiment 85 includes the computer program product of any of embodiments 80 through 84 or any of embodiments 86 through 89, comprising further computer instructions for one of automatically activating the exercise mode and prompting the user to manually activate the exercise mode in response to receiving data from a GPS module of the user's mobile communication device indicating device proximity to a location in which the exercise mode has been previously activated.

Embodiment 85 includes the computer program product of any of embodiments 80 through 85 or any of embodiments 87 through 89, comprising further computer instructions for maintaining the activation of the exercise mode for a fixed period of time.

Embodiment 87 includes the computer program product of any of embodiments 80 through 86 or any of embodiments 88 or 89, wherein the exercise mode is adjustable for at least one of type and intensity of exercise.

Embodiment 88 includes the computer program product of any of embodiments 80 through 87 or embodiment 89, comprising further computer instructions for: monitoring and recording user blood glucose response data during a particular exercise activity; reviewing recorded user blood glucose response data collected during past occurrences of the particular exercise activity; and retroactively calculating the optimal parameters for a pre-exercise glucose management recommendation based upon the review of the past blood glucose response data for a particular exercise activity.

Embodiment 89 includes the computer program product of any of embodiments 80 through 88, comprising further computer instructions for: gauging success of exercise mode usage after a completed exercise event; and incrementally adjusting pre-exercise glucose management recommendation parameters based on the success outcome.

Embodiment 90 includes a computer program product installable on a mobile communication device and configured for use with a peripheral electronic medical device in wireless communication with the mobile communication device, the computer program product embodied in a non-transitory computer readable storage medium and comprising a dose calculator module including computer instructions for: analyzing blood glucose data to establish dose calculator module parameters comprising a blood glucose correction parameter, a carbohydrates cover parameter, an insulin on board parameter, and a glucose trend adjustment parameter; calculating an insulin dose recommendation based upon the analyzed blood glucose data and established dose calculator parameters; and activating a conservative mode wherein the glucose trend adjustment parameter is adjusted to avoid hypoglycemia.

Embodiment 91 includes the computer program product of embodiment 90 or any of embodiments 92 through 97, wherein the glucose trend adjustment parameter is reduced by a fixed offset amount.

Embodiment 92 includes the computer program product of embodiments 90 or 91 or any of embodiments 93 through 97, wherein the glucose trend adjustment parameter is reduced by a percentage amount.

Embodiment 93 includes the computer program product of any of embodiments 90 through 92 or any of embodiments 94 through 97, wherein the glucose trend adjustment parameter is reduced by the greater of a fixed offset amount and a percentage amount.

Embodiment 94 includes the computer program product of any of embodiments 90 through 93 or any of embodiments 95 through 97, wherein the glucose trend adjustment parameter is limited to a maximum amount of influence.

Embodiment 95 includes the computer program product of any of embodiments 90 through 94 or any of embodiments 96 or 97, wherein the glucose trend adjustment parameter is limited to a greater degree when applied to increasing insulin than when applied to decreasing insulin.

Embodiment 96 includes the computer program product of any of embodiments 90 through 95 or embodiment 97, wherein upon establishing confidence in dose calculator parameters after a period of continued use, the computer program product comprises further computer instructions for: removing restrictions on glucose trend adjustment parameter values; and limiting carbohydrates cover value to a maximum influence recommendation.

Embodiment 97 includes the computer program product of any of embodiments 90 through 96, wherein upon establishing confidence in dose calculator parameters after a period of continued use, the computer program product comprises further computer instructions for: scaling restrictions on glucose trend adjustment parameter values based on the established confidence rating; and limiting carbohydrates cover value to a maximum influence recommendation.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing unit" or "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

It is intended that the specification, together with the drawings, be considered exemplary only, where exemplary means an example. As used herein, the singular forms "a", "an" and "the" are intended to include the plural forms as well, unless the context clearly indicates otherwise. Additionally, the use of "or" is intended to include "and/or", unless the context clearly indicates otherwise.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A method for determining a recommended dose of insulin to administer to a user of an insulin delivery device using a dose calculator, comprising:

determining a plurality of dose calculator parameters for a patient user of an insulin delivery device, including a blood glucose correction parameter, a carbohydrates cover parameter, an insulin on board (IOB) parameter, a glucose trend adjustment parameter, and a carbohydrates on board (COB) adjustment parameter for the patient user, wherein:

the COB adjustment parameter includes a quotient of an estimated value for unmetabolized carbohydrates ingested from recent meals by the patient user and an insulin-to-carbohydrates ratio of the patient user; and the blood glucose correction parameter includes a difference value between a current glucose level of the patient user and a quotient of a target glucose level and a sensitivity factor of the patient user;

calculating an insulin dose recommendation based on an estimated sum of the blood glucose correction parameter, the glucose trend adjustment parameter, the carbohydrates cover parameter and the COB adjustment parameter subtracted by the IOB parameter;

determining a confidence value for the glucose trend adjustment parameter, wherein determining the confidence value includes, for each use of the dose calculator:

predicting a blood glucose response after administration of the insulin dose recommendation;

determining a measured blood glucose response after administration of the insulin dose recommendation;

determining a percent error based on a difference between the predicted blood glucose response and the measured blood glucose response; and determining the confidence value based on a running average of the percent error over a plurality of uses of the dose calculator;

comparing the confidence value to a minimum threshold confidence value;

omitting the glucose trend adjustment parameter from the calculation of the insulin dose recommendation until a minimum number of uses of the dose calculator is achieved and the confidence value attains the minimum threshold confidence value; and administering the calculated insulin dose recommendation with the insulin delivery device.

2. The method of claim 1, wherein the estimated value for unmetabolized carbohydrates of the COB adjustment parameter includes a carbohydrates burndown parameter.

3. The method of claim 2, wherein the carbohydrates burndown parameter comprises a fixed time period after a last ingested meal by the patient user during which carbohydrates are typically expected to be metabolized.

4. The method of claim 2, wherein the carbohydrates burndown parameter includes a variable value associated with a metabolism rate of specific carbohydrates.

5. The method of claim 2, wherein the carbohydrates burndown parameter includes a qualitative value associated with at least one of a fast burndown rate and a slow burndown rate.

6. The method of claim 2, wherein the carbohydrates burndown parameter includes an estimated value based on a population data for a particular type of food.

7. The method of claim 2, wherein the carbohydrates burndown parameter is determined by:

assigning the carbohydrates burndown parameter a value corresponding to a first predetermined burndown rate associated with a fast metabolic rate of carbohydrate for a first portion of a time period after a last ingested meal by the patient user; and assigning the carbohydrates burndown parameter a value corresponding to a second predetermined burndown rate associated with a slow metabolic rate of carbohydrate for a second portion of the time period.

8. The method of claim 2, wherein the carbohydrates burndown parameter is determined by:

assigning the carbohydrates burndown parameter a value corresponding to a first predetermined burndown rate associated with a fast metabolic rate of carbohydrate for a first portion of a time period after a last ingested meal by the patient user; and assigning the carbohydrates burndown parameter a value corresponding to a second burndown rate, wherein the second burndown rate is determined based on a net carbohydrates response estimation using an initial blood glucose value, a rate of change of the blood glucose levels over a second portion of the time period, and a current blood glucose value of the patient user.

9. The method of claim 1, wherein the carbohydrates cover parameter includes a quotient of a carbohydrates value and the insulin-to-carbohydrates ratio of the patient user.

10. The method of claim 1, wherein the IOB parameter includes an estimated value of remaining units of insulin in the patient user's body.

11. The method of claim 1, wherein the glucose trend adjustment parameter comprises an estimated value of a rate of change in glucose levels of the patient multiplied by a projection time and then divided by an insulin sensitivity factor (ISF) of the patient user.

12. The method of claim 1, further comprising:

determining a confidence value for each of the dose calculator parameters.

13. The method of claim 1, further comprising:

displaying the produced insulin dose recommendation on at least one of a display unit of the insulin delivery device and a display unit of a mobile device in wireless communication with the insulin delivery device.

14. The method of claim 13, wherein the mobile device is implemented on one or more of a smartphone, a tablet, a smartwatch, a smartglasses, a wearable device, or a laptop or a desktop computer.

15. The method of claim 1, wherein at least one of the IOB parameter and the COB adjustment parameter comprises a projected future value.

16. The method of claim 1, wherein the glucose trend adjustment parameter is enabled for downward trends and disabled for upward trends.

17. The method of claim 1, wherein the glucose trend adjustment parameter is enabled for downward trends and upward trends to a predetermined threshold value.

18. The method of claim 1, wherein the glucose trend adjustment parameter is enabled for downward trends and enabled for upward trends, and a scaling factor is applied to upward trends.

19. A system, comprising:

a processor configured to provide a calculated insulin dose recommendation to an insulin delivery device; and a memory storing instructions, which when executed by the processor, cause the performance of a method comprising:

determining a glucose trend adjustment parameter for the insulin delivery device using a dose calculator;

calculating the insulin dose recommendation based on an estimated sum of a plurality of dose parameters for the insulin delivery device including the glucose trend adjustment parameter;

determining a confidence value for the glucose trend adjustment parameter, wherein determining the confidence value includes:

predicting a blood glucose response after administration of the insulin dose recommendation;

determining a measured blood glucose response after administration of the insulin dose recommendation;

determining a percent error based on a difference between the predicted blood glucose response and the measured blood glucose response; and determining the confidence value based on a running average of the percent error over a plurality of uses of the dose calculator;

comparing the confidence value to a minimum threshold confidence value; and omitting the glucose trend adjustment parameter from the calculation of the insulin dose recommendation until a minimum number of uses of the dose calculator is achieved and the confidence value attains the minimum threshold confidence value; and providing the calculated insulin dose recommendation to the insulin delivery device for administering insulin using the insulin delivery device; and the insulin delivery device configured to deliver the calculated insulin dose recommendation provided by the processor.

* * * * *